(12) United States Patent
Schmitz et al.

(10) Patent No.: US 9,155,695 B2
(45) Date of Patent: Oct. 13, 2015

(54) INJECTABLE ROPINIROLE COMPOSITIONS AND METHODS FOR MAKING AND USING SAME

(71) Applicant: Medtronic, Inc., Minneapolis, MN (US)

(72) Inventors: Michael C. Schmitz, Prior Lake, MN (US); Roger E. Harrington, Collierville, TN (US); Carmen E. Snaza, Maplewood, MN (US); Keith R. Hildebrand, Houlton, WI (US); Ngoc N. Lu, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 120 days.

(21) Appl. No.: 13/828,148

(22) Filed: Mar. 14, 2013

(65) Prior Publication Data

US 2014/0275202 A1    Sep. 18, 2014

(51) Int. Cl.

| | | |
|---|---|---|
| *A01N 43/38* | (2006.01) | |
| *A61K 31/40* | (2006.01) | |
| *A61K 9/00* | (2006.01) | |
| *A61K 31/4045* | (2006.01) | |
| *A61K 9/19* | (2006.01) | |
| *A61K 47/12* | (2006.01) | |

(52) U.S. Cl.
CPC .............. *A61K 9/0019* (2013.01); *A61K 9/19* (2013.01); *A61K 31/4045* (2013.01); *A61K 47/12* (2013.01)

(58) Field of Classification Search
CPC . A61K 31/4045; A61K 47/12; A61K 9/0019; A61K 9/19
See application file for complete search history.

(56) References Cited

U.S. PATENT DOCUMENTS

| | | |
|---|---|---|
| 4,452,808 A | 6/1984 | Gallagher, Jr. |
| 6,218,421 B1 | 4/2001 | King |
| 6,423,351 B2 | 7/2002 | Wang |
| 7,306,497 B2 | 12/2007 | Buzzi |
| 7,309,497 B2 | 12/2007 | Rimpler et al. |
| 7,318,936 B2 | 1/2008 | Ding et al. |
| 7,927,624 B2 | 4/2011 | Vergnault et al. |
| 8,277,845 B2 | 10/2012 | Jacobson |
| 8,283,380 B2 | 10/2012 | Fariello et al. |
| 8,304,429 B2 | 11/2012 | Boyd et al. |
| 2008/0280980 A1 | 11/2008 | Van Dyke |
| 2011/0118850 A1 | 5/2011 | Govil et al. |
| 2011/0262537 A1 | 10/2011 | Nakhat et al. |
| 2012/0157965 A1 | 6/2012 | Wotton et al. |

FOREIGN PATENT DOCUMENTS

WO    WO2005080333 A1 * 9/2005

OTHER PUBLICATIONS

Nema (Encyclopedia of Pharmaceutical Technology, 2007, p. 1622-1645).*

* cited by examiner

*Primary Examiner* — Uma Ramachandran
(74) *Attorney, Agent, or Firm* — William D. Schmidt; Sorell, Lenna & Schmidt, LLP

(57) ABSTRACT

Compositions and methods are provided that utilize an injectable ropinirole having a therapeutically effective amount of ropinirole in an aqueous solvent, the composition having a pH of from about 3.0 to about 6.5. The compositions and methods provided contain less than 3% by weight of impurities and are suitable for administration by infusion pumps. In some embodiments, the compositions are made in an oxygen free environment and/or are made with an antioxidant to reduce impurities and improve stability. In some embodiments, the compositions provided are utilized to treat Parkinson's disease.

23 Claims, 14 Drawing Sheets

INJECTABLE ROPINIROLE COMPOSITIONS AND METHODS FOR MAKING AND USING SAME

FIELD

This application relates to, among other things, stable and injectable compositions comprising ropinirole and methods of making and using them.

BACKGROUND

Parkinson's disease is the second most prevalent neurodegenerative disease. There are over 4 million patients in the world and the incidence rate is rapidly increasing with a rising elderly population. The symptoms of Parkinson's disease typically show progressive locomotive defects such as rigidity, tremor, bradykinesia of the limbs, and postural instability, and non-locomotive defects such as cognitive dysfunction, depression, sleep disorder, and pain.

In the aspect of anatomy, selective degeneration of dopaminergic neurons in the substantia nigra is the pathological hallmark of Parkinson's disease. When 60-80% of dopaminergic neurons in the substantia nigra are decreased, extrapyramidal tracts cannot efficiently work and the symptoms of Parkinson's disease occur.

Parkinson's disease is currently treated using dopamine replacement therapies. Because of the loss of dopamine-containing neurons in the brain, oral levodopa and dopamine agonist drugs are mainstay therapies for Parkinson's disease. These drugs are generally administered several times a day or more to increase dopamine levels in the brain. One oral formulation that is administered three to four times a day is the combination of levodopa and carbidopa.

However, the blood levels resulting from oral administration may often fluctuate between high blood concentrations (e.g., peaks) that are often associated with side effects such as dyskinesias (e.g., diminished voluntary movements and the presence of involuntary movements) and low blood levels (e.g., troughs) that are often associated with return of the motor symptoms ("off" time) of Parkinson's disease. As the disease progresses and oral drug therapy is continued, the peak-trough effects may become more exaggerated and severe leading to poor patient compliance.

To counter the peak-trough effects of short acting oral formulations, sustained release oral formulations are currently available to treat Parkinson's disease. Sustained release oral ropinirole is an example of one such formulation, which is marketed by GlaxoSmithKline under the name Requip XL®. This sustained release formulation is administered less frequently than the oral immediate release formulation and generally contributes to better patient compliance.

However, Parkinson's disease patients often have dysfunctional gastric motility, especially as the disease progresses, which can lead to delayed emptying of the stomach and delayed absorption of the oral formulation and thus a delayed onset of dopaminergic symptom relief.

It would therefore be desirable to provide injectable ropinirole compositions and methods that do not rely on a functioning gastrointestinal tract for efficacy. Injectable ropinirole compositions and methods that are stable for extended periods of time and that can be administered by an infusion would also be beneficial in the treatment of Parkinson's disease.

SUMMARY

New injectable ropinirole compositions and methods are provided that do not rely on a functioning gastrointestinal tract for efficacy. Injectable ropinirole compositions and methods are provided that have low impurities (e.g., less than 3%) and are stable for extended periods of time even after steam sterilization and/or lyophilization.

These injectable ropinirole compositions can be made by reducing or preventing oxidation of the ropinirole by adding an antioxidant and/or by manufacturing in a reduced oxygen environment. The injectable ropinirole compositions provided, in some embodiments, can be administered by continuous infusion so as to reduce or eliminate the drug fluctuations associated with oral Parkinson's disease therapies.

In one embodiment, there is an injectable ropinirole composition comprising a therapeutically effective amount of ropinirole in an aqueous solvent, the composition having a pH of from about 3.0 to about 6.5. The ropinirole composition can be lyophilized and/or can contain an antioxidant to reduce formation of impurities in the composition on manufacture and storage.

In a second embodiment, there is an injectable ropinirole composition comprising a therapeutically effective amount of lyophilized ropinirole in powdered form and comprising less than 3% by weight of (4-[2-(dipropylamino)ethyl]indoline-2,3-dione hydrochloride).

In one exemplary embodiment, there is a method of preparing a terminally sterilized injectable ropinirole composition, the method comprising adjusting the pH of ropinirole in an aqueous solvent to between about 3.0 to about 6.5, wherein the concentration of ropinirole in the aqueous solvent is between 0.05 mg/mL and 133 mg/mL; and heat sterilizing the pH-adjusted ropinirole to achieve a sterility assurance level of $1\times10^6$ or $1\times10^{12}$ so as to form a terminally sterilized injectable ropinirole composition having less than 3% by weight of (4-[2-(dipropylamino)ethyl]indoline-2,3-dione hydrochloride) based on a total weight of the composition.

In another exemplary embodiment, there is a method of preparing a lyophilized injectable ropinirole composition, the method comprising adjusting the pH of ropinirole in an aqueous solvent to between about 3.0 to about 6.5, wherein the concentration of ropinirole in the aqueous solvent is between 0.05 mg/mL and 133 mg/mL; and lyophilizing the pH-adjusted ropinirole so as to form the injectable lyophilized ropinirole composition.

In some embodiments, there is a method of reducing formation of (4-[2-(dipropylamino)ethyl]indoline-2,3-dione hydrochloride) in an injectable ropinirole composition, the method comprising adjusting the pH of ropinirole in an aqueous solvent to between about 3.0 to about 6.5, wherein the concentration of ropinirole in the aqueous solvent is between 0.05 mg/mL and 133 mg/mL and the composition comprises less than 3% by weight of (4-[2-(dipropylamino)ethyl]indoline-2,3-dione hydrochloride) based on a total weight of the composition.

In some embodiments, there is a method of treating Parkinson's disease in a patient suffering therefrom, the method comprising administering an injectable ropinirole composition comprising a therapeutically effective amount of ropinirole in an aqueous solvent, the composition having a pH of from about 3.0 to about 6.5.

In some embodiments, the injectable ropinirole composition may: (i) consist of only the ropinirole (or one or more of its pharmaceutically acceptable salts), the aqueous solvent, and buffering agent(s); or (ii) consist essentially of the ropinirole (and/or one or more of its pharmaceutically acceptable salts), the aqueous solvent, and buffering agent(s); or (iii) comprise the ropinirole (and/or one or more of its pharmaceutically acceptable salts), the aqueous solvent, and buffering agent(s) and one or more other active ingredients, surfactants, excipients or other ingredients or combinations thereof. When there are other active ingredients, surfactants, excipients or other ingredients or combinations thereof in the composition, in some embodiments these other compounds or combinations thereof comprise less than 50 wt. %, less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

DETAILED DESCRIPTION

Figure 1:
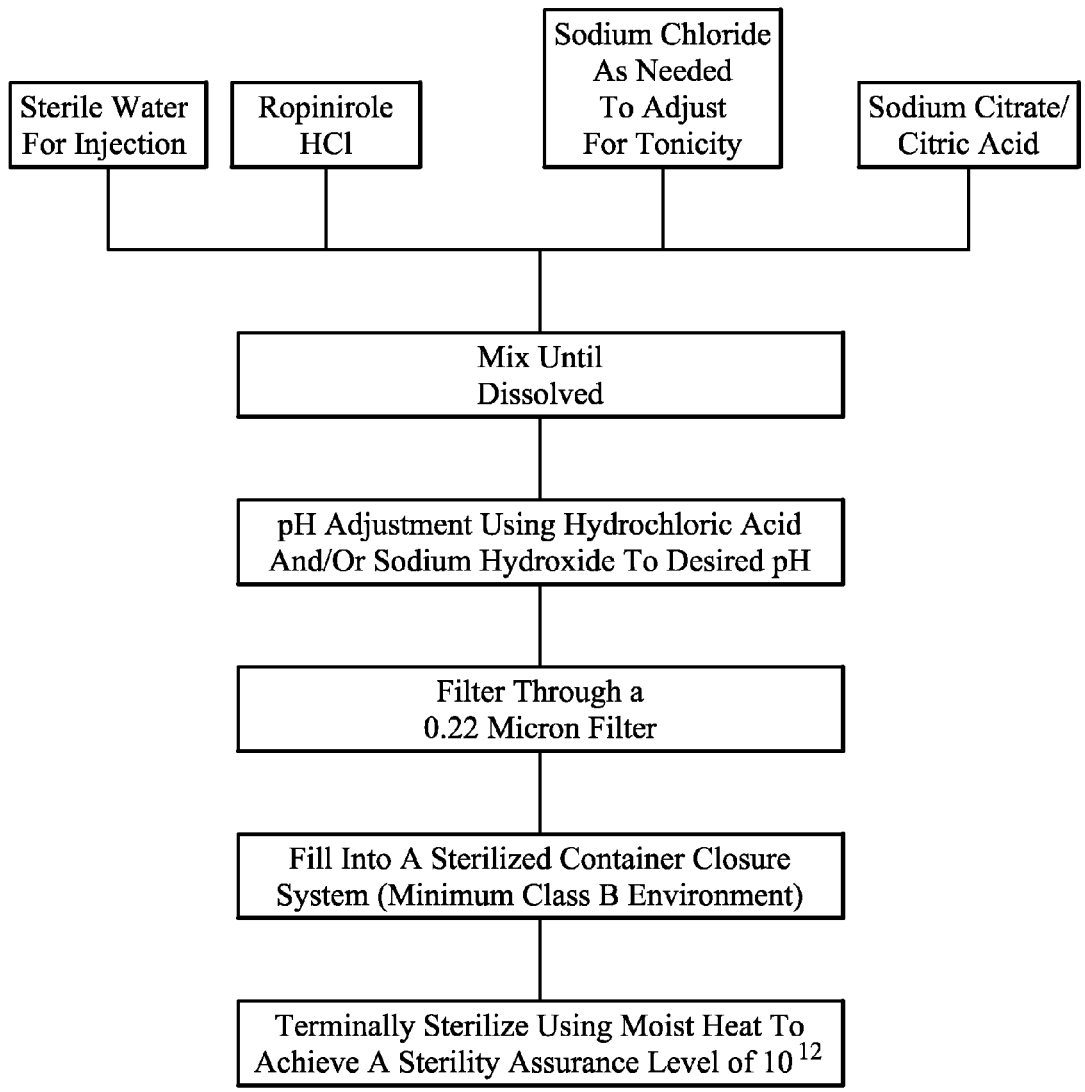
FIG. 1 is a flow diagram illustrating the steps to make sterilized ropinirole injection in accordance with one embodiment of the disclosure.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

All scientific and technical terms used herein have meanings commonly used in the art unless otherwise specified. The definitions provided herein are to facilitate understanding of certain terms used frequently herein and are not meant to limit the scope of the present disclosure.

It is noted that, as used in this specification and the appended claims, the singular forms "a," "an," and "the," include plural referents unless expressly and unequivocally limited to one referent. Thus, for example, reference to "an antioxidant" includes one, two, three or more antioxidants.

As used in this specification and the appended claims, the term "or" is generally employed in its sense including "and/or" unless the content clearly dictates otherwise.

The phrase "injectable" or "injectable composition," as used herein, means a composition that can be drawn into a container and injected intravenously, subcutaneously, intramuscularly, intra-arterially, inthrathecally, epidurally, intraparenchymally, intraperitoneally, intracerebroventricularly, intraventricularly, or the like into an animal.

The headings below are not meant to limit the disclosure in any way; embodiments under any one heading may be used in conjunction with embodiments under any other heading.

Ropinirole

New injectable ropinirole compositions and methods provided do not rely on a functioning gastrointestinal tract of a patient for efficacy. Injectable ropinirole compositions and methods provided have low impurities (e.g., less than 3%) and are stable for extended periods of time even after steam sterilization and/or lyophilization. These injectable ropinirole compositions can be made by reducing or preventing oxidation of the ropinirole by adding an antioxidant and/or by manufacturing in a reduced oxygen environment. The injectable ropinirole compositions provided, in some embodiments, can be administered by continuous infusion so as to reduce or eliminate the drug fluctuations associated with oral Parkinson's disease therapies.

Ropinirole is a non-ergoline dopamine agonist. Ropinirole is disclosed in U.S. Pat. No. 4,452,808 the entire disclosure is herein incorporated by reference into the present disclosure. Ropinirole exhibits the following structure:

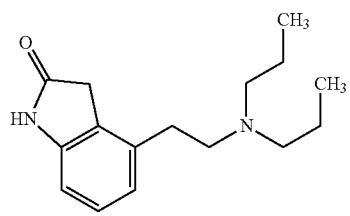 [SMILES: CCCN(CCC)CCc1cccc2c1CC(=O)N2]

Ropinirole is available as the hydrochloride salt of 4-[2-(dipropylamino)ethyl]-1,3-dihydro-2H-indol2-one monohydrochloride and exhibits the following structure:

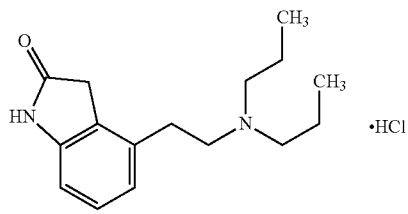 [SMILES: CCCN(CCC)CCc1cccc2c1CC(=O)N2 ; Cl]

Ropinirole hydrochloride has the molecular formula $C_{16}H_{24}N_2O \cdot HCl$ and a molecular weight of 296.84, while the free base has a molecular weight of 260.38.

As used herein ropinirole includes polymorphs, pharmaceutically acceptable salts, solvates, esters, or hydrates thereof. The phrase "pharmaceutically acceptable salt(s)", as used herein, means those salts of compounds of the disclosure that are safe and effective for use in mammals and that possess the desired biological activity.

Pharmaceutically acceptable salts of ropinirole include any acid addition or base addition salt that retains the biological activity and properties of the corresponding free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the like). Base addition salts can be formed with inorganic bases (e.g., sodium, potassium, lithium, ammonium, calcium, magnesium, zinc, aluminum salts, and the like) and organic bases (e.g., salts of primary, secondary, and tertiary amines, substituted amines including naturally-occurring substituted amines, cyclic amines and basic ion exchange resins, such as isopropylamine, trimethylamine, diethylamine, triethylamine, tripropylamine, ethanolamine, 2-dimethyl-aminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, or the like). In one embodiment, the ropinirole comprises ropinirole hydrochloride.

The ropinirole used in the composition can be micronized before it is mixed with solvents and other excipients. In various embodiments, the particle size of the ropinirole can range from about 1 micron to 250 microns. In some embodiments, the ropinirole can have a particle size of from about 5 microns to about 100 microns or from about 20 to 50 microns.

Injectable ropinirole compositions and methods provided have low impurities (e.g., less than 3%) and are stable for extended periods of time even after heat sterilization and/or lyophilization.

The ropinirole can be in the composition at a concentration of from about 1 mg/mL to about 133 mg/mL. In some embodiments, the ropinirole can be in the composition in an amount of 0.05, 0.5, 1, 5, 10, 15, 20, 25, 30, 35, 40, 45, 50, 55, 60, 65, 70, 80, 85, 90, 95, 100, 105, 110, 115, 120, 125, 130, or 133 mg/mL.

The ropinirole can be mixed with a suitable aqueous solvent that dilutes, dissolves and/or suspends the ropinirole. The aqueous solvent of interest is one which is pharmaceutically acceptable (safe and non-toxic for administration to a human) and is useful for the preparation of a reconstituted formulation. Exemplary aqueous solvents include sterile water, sterile water for injection (SWFI), bacteriostatic water for injection (BWFI), a pH-buffered solution (e.g., phosphate-buffered saline), sterile saline solution, Ringer's solution or dextrose solution.

In some embodiments, the ropinirole can be mixed with a suitable non-aqueous solvent that dilutes, dissolves and/or suspends the ropinirole. The non-aqueous solvent of interest is one which is pharmaceutically acceptable (safe and non-toxic for administration to a human) and is useful for the preparation of a reconstituted formulation. Exemplary non-aqueous solvents include polyethylene glycol, or ethyl alcohol.

Excipients

While the injectable ropinirole compositions provided may contain any of a number of known pharmaceutical additives or excipients, in many embodiments, the injectable ropinirole compositions contain as few ingredients or components as possible to achieve a desired pH, stability (e.g., low or no impurities), solubility, tonicity and/or ionic strength.

By controlling the pH of the ropinirole in an aqueous solvent and/or reducing oxidation of the ropinirole in the manufacturing process, injectable ropinirole compositions can be made that have low impurities (less than 3%).

Impurities may occur when making ropinirole injection and/or on storage of it. Impurities include substances unintentionally present in the composition that are not the ropinirole itself or the excipients (e.g., buffers, anti-oxidants, pH adjustment agents, bulking agent, solvent, preservatives, etc.) used to manufacture it. These impurities include, for example, 4-(2-hydroxyethyl)indolin-2-one (USP Ropinirole Related Compound A), 4-[2-(dipropylamino)ethyl]indoline-2,3-dione hydrochloride (USP Ropinirole Related Compound B), 4-[2-(Propylamino)ethyl]-1,3-dihydro-2H-indol-2-one hydrochloride (API process impurity), 4-[2-Ethylpropylamino)ethyl]-1,3-dihydro-2H-indol-2-one hydrochloride (Active Pharmaceutical Ingredient process impurity), combinations thereof, other degradation product, microbes, and/or particulates.

It has been found, in some embodiments, that by controlling the pH before heat sterilization (e.g., steam sterilization) and/or lyophilization that injectable ropinirole compositions can be made that are stable and have a low level of impurities (e.g., less than about 3%). The injectable ropinirole composition is essentially free or free from impurities. However, during manufacturing and/or storage at room temperature or under refrigeration, impurities may be generated. In some embodiments, the impurities are in the composition in an amount that is less than 3.0, 2.5, 2.0, 1.5, 1.0, 0.5, 0.3, 0.25, 0.2, 0.15, 0.1, 0.05, 0.04, 0.03, 0.02, 0.01, or 0.001 weight percent based on the total weight of the composition or the weight of the ropinirole in the composition.

Figure 3A:
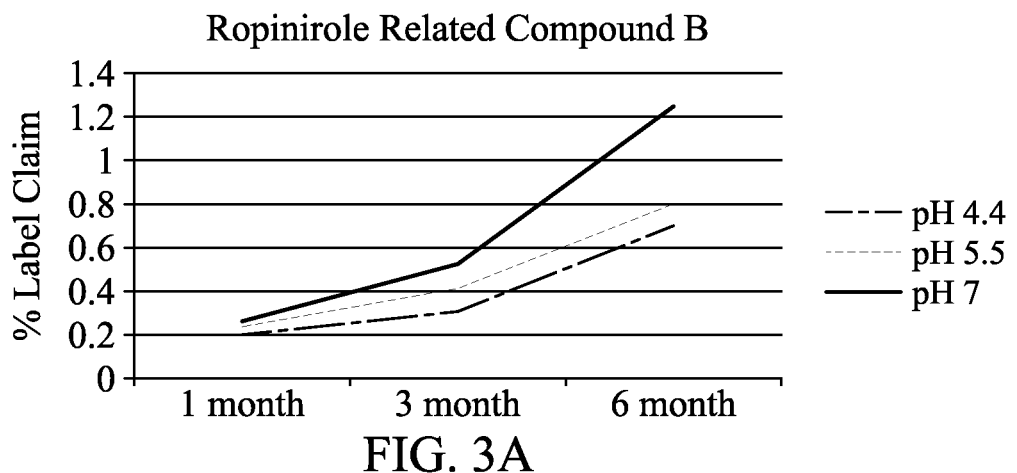
FIGS. 3A-3C are graphic illustrations showing the pH effect and the generation of impurities for sterilized injectable ropinirole.
Figure 3B:
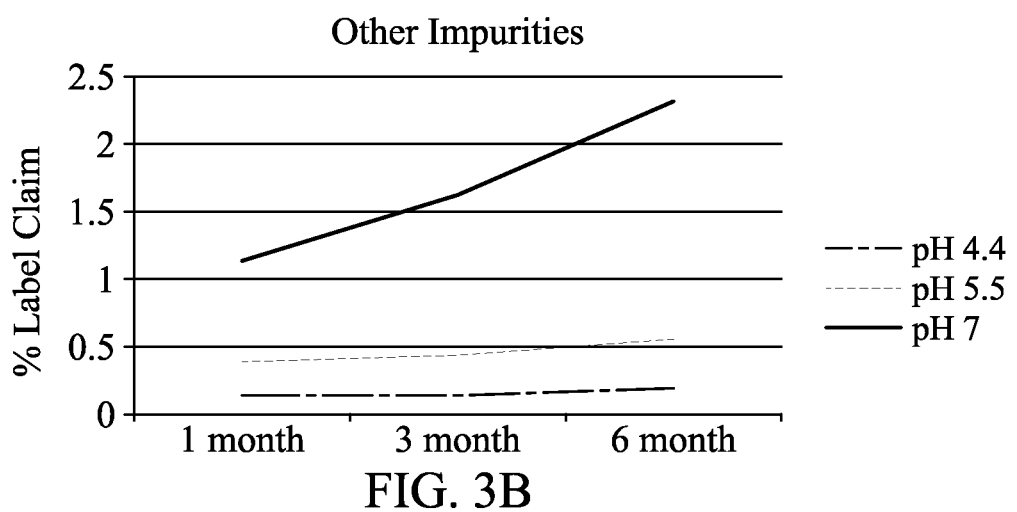
Figure 3C:
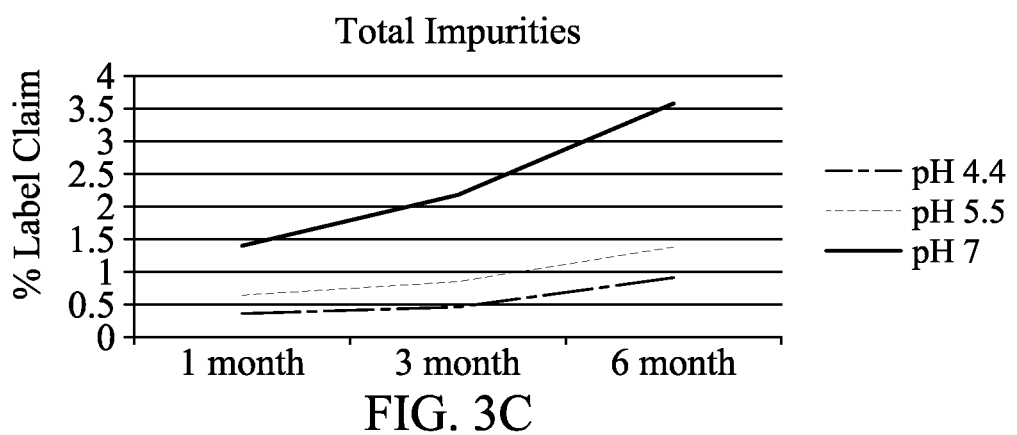

In some embodiments, the pH of the ropinirole composition can range from about 3.5 to about 6.5 for stable injectable ropinirole. Therefore, the pH can range from about 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, to about 6.5. As the pH approaches 7.0, the impurities increase as shown in FIGS. 3A-3C over a period of from about 1 month to about 6 months.

The pH of the ropinirole in an aqueous solvent can be adjusted using a pH adjustment agent. Suitable pH adjustment agents include, but are not limited to, sodium hydroxide, potassium hydroxide, tromethamine, monoethanolamine, potassium citrate, triethanolamine, sodium citrate, sodium chloride, diethanolamine, sodium bicarbonate, hydrochloride acid, sulfuric acid, phosphoric acid, citric acid, tartaric acid, lactic acid, sodium lactate or a combination thereof. The citric acid and/or the citrate, in some embodiments can function as both a buffer and an antioxidant.

The ropinirole can be mixed, in some embodiments, with a buffering agent to prevent or reduce pH changes on manufacture and/or storage. The buffering agent can be, for example, phosphate, citrate, tartrate, acetate or the like. The buffer can be for example, phosphate-buffered saline, which is a water-based salt solution containing either sodium chloride or potassium chloride, sodium phosphate or potassium phosphate. In some embodiments, the buffering agent can comprise sodium citrate, sodium acetate, sodium phosphate, and/or combinations thereof. In one particular embodiment, the buffering agent can comprise sodium citrate dihydrate, and citric acid monohydrate. The citric acid and/or the citrate, in some embodiments, can function as both a buffer and an antioxidant. Typically, the buffering agent is added to the composition in quantities of from about 0.01% to about 20% by weight. In some embodiments, the buffering agent can be in the composition in an amount of from about 0.1%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4.0%, 4.5% to about 5% by weight. In some embodiments, the buffering agent can be in the composition in an amount of from about 1% to about 3% by weight.

In some embodiments, a bulking agent can be used in the composition so that the ropinirole can be made in a conveniently administered injection. Suitable bulking agents include, but are not limited to, hydrophilic excipients, such as, sodium chloride, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, talc, zinc oxide, starch, hydroxyethylstarch (hetastarch), cellulose, cyclodextrins, glycine, fructose, gulose, idose, galactose, talose, ribose, arabinose, raffinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and/or mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats or polyvinylpyrrolidone or a combination thereof. Exemplary bulking agents include mannitol, glucose, trehalose, sorbitol, sodium chloride, or any combination thereof such bulking agent.

The ropinirole composition, in some embodiments, can have a tonicity agent included in it for injection. The term "tonicity agent" as used herein denotes a pharmaceutically acceptable excipient used to modulate the tonicity of a composition. Tonicity in general relates to the osmotic pressure of a solution usually relative to that of human blood. Suitable tonicity agents include, but are not limited to, sucrose, mannitol, sorbitol, water-based salt solution containing sodium chloride, potassium chloride, sodium phosphate, potassium phosphate, sodium citrate, sodium acetate, and/or combinations thereof. In some embodiments, the tonicity of the ropinirole composition can be between about 270 mOsm and 315 mOsm, e.g., between about 285 mOsm and 315 mOsm.

The ropinirole composition, in some embodiments, may also include a preservative suitable for injection. Suitable preservatives for use include, but are not limited to, benzalkonium chloride, methyl, ethyl, propyl or butylparaben, benzyl alcohol, phenylethyl alcohol, benzethonium, thimerosal, or a combination thereof.

In some embodiments, the ropinirole (e.g., containing buffering agent, bulking agent, pH adjustment agent, antioxidant, etc.) can be filtered by passing the ropinirole and solvent through a filter (e.g., 0.22 microns). This will remove bacteria and other larger-size particulates out of the composition. In one embodiment, the pH of the ropinirole in an aqueous solvent is between about 4.0 and 6.5, before it is filtered.

After the ropinirole composition is filtered, in some embodiments, the ropinirole is terminally sterilized. As used herein, "sterilized" includes that the ropinirole composition is essentially free or free of viable microorganisms (e.g., bacteria, viruses, fungi, etc.) and their spores. Often sterility assurances levels of at least $1\times10^6$ are needed for terminal sterility. In various embodiments, the compositions are sterilized by heat treatment, such as steam sterilization or autoclaving. In some embodiments, heat treatment, regardless of temperature, time or type, which results in a $1\times10^6$ sterility assurance level (the probability that a given unit is not sterile is one in a million) is used. In some embodiments, the ropinirole has a sterility assurance level of $1\times10^{12}$. In some embodiments, the ropinirole compositions are heat sterilized at 121° C. to achieve a sterility assurance of $1\times10^{12}$.

Heat sterilization may result in increased production of impurities (e.g., 4-[2-(dipropylamino)ethyl]indoline-2,3-dione hydrochloride (USP Ropinirole Related Compound B)). By adjusting pH to from about 3.5 to about 6.5, stable sterilized injectable ropinirole compositions can be produced. In one embodiment, the pH is kept between about 4.0 to about 6.0 to reduce the formation of impurities on manufacture and storage.

In one embodiment, there is a method of reducing formation of (4-[2-(dipropylamino)ethyl]indoline-2,3-dione hydrochloride) in an injectable ropinirole composition, the method comprising adjusting a pH of ropinirole in an aqueous solvent to between about 3.0 to about 6.5, wherein the concentration of ropinirole in the aqueous solvent is between 0.05 mg/mL and 133 mg/mL and the composition comprises less than 3% by weight of (4-[2-(dipropylamino)ethyl]indoline-2,3-dione hydrochloride) based on a total weight of the composition or the total weight of the ropinirole being used.

FIG. 1 is a flow diagram illustrating the steps to make sterilized ropinirole injection in accordance with one embodiment of the disclosure. The ropinirole is mixed with SWFI as the aqueous solvent, sodium chloride to adjust tonicity, and sodium citrate/citric acid as the buffer/antioxidant. Typically, in this embodiment, the pH is about 4.1 or about 4.2. The pH of the mixture is then adjusted with for example, hydrochloric acid and/or sodium hydroxide to the desired pH, which in this embodiment is about 4.4 to about 4.5. The pH adjusted mixture is then filtered through a 0.22 micron filter to remove bacteria, other microbes, larger viruses and/or particulates. The filtered solution is then placed in a container suitable to store the composition and then the composition is terminally sterilized.

An exemplary sterilized ropinirole composition suitable for injection is listed in the Table A below.

TABLE A

Sterile Liquid Ropinirole Composition

| Ingredient | Purpose | Concentration mg/mL |
|---|---|---|
| Ropinirole HCl | API | 15.0 |
| Citric Acid | Buffer/Antioxidant | 1.1 |
| Sodium Citrate | Buffer | 1.4 |
| Sodium Chloride | Tonicity adjustment | 6.0 |
| NaOH | pH adjustment | For pH adjustment |
| HCl | pH adjustment | For pH adjustment |
| Water for Injection | Solvent | QS to 1 mL |

The impurities generated and its stability over 3, 6, 9, 12, 15, and 18 months are shown in FIGS. 9A-9D. It is contemplated that the formulations will be stable for longer periods of time in sterilized and injectable form, for example, 2 years, 3 years or longer. This is particularly so if the compositions are made in a low oxygen environment, an anti-oxidant is used, and/or the compositions are lyophilized.

Reducing Oxidation

It has also been found that, in some embodiments, ropinirole degradation is due to oxidation of the composition. Reducing the oxidation of ropinirole during manufacture and storage will allow injectable ropinirole compositions that have low impurities (less than 3%). It is believed that ropinirole undergoes oxidation, in some embodiments, according to reaction scheme I below.

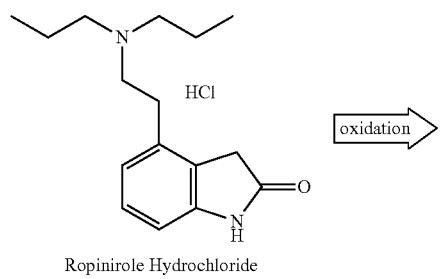

Ropinirole Hydrochloride

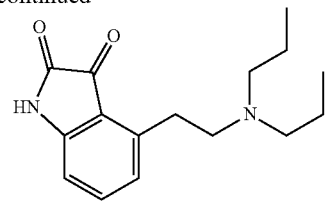

USP Ropinirole Related Compound B (4-[2-(dipropylamino)ethyl]indoline-2,3-dione hydrochloride) (USP Ropinirole Related Compound B above) is an example of an impurity that forms based in part on oxidation of ropinirole.

In some embodiments, to reduce the formation of impurities (e.g., USP Ropinirole Related Compound B), the composition can contain an antioxidant that is suitable for injection and that reduces and/or prevents oxidation of ropinirole. Oxidation can produce free radicals, which start chain reactions that can have adverse effects on the purity and stability of the formulation. Antioxidants terminate these chain reactions by removing free radical intermediates, and inhibit other oxidation reactions by being oxidized themselves. Suitable antioxidants for use in the ropinirole compositions include, but are not limited to, sulfites like sodium sulfite, sodium bisulfite, sodium metabisulfite, sodium formaldehyde sulfoxylate, thiourea, sequestering agents such as sodium salt of ethylenediaminetetraacetic acid (EDTA) or acids such as citric acid, ascorbic acid, sodium citrate, or a combination thereof. The antioxidant is added to the composition in quantities of from about 0.1%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4.0%, 4.5% to about 5% by weight. In some embodiments, the antioxidant can be in the composition in an amount of about 1% to about 20% by weight. In other embodiments, the antioxidant can be present in the composition in an amount of about 1% to about 3% by weight. FIGS. 4-8C are graphic illustrations showing the generation of impurities for sterilized injectable ropinirole compositions comprising different antioxidants. The addition of citrate buffer and/or citric acid to the ropinirole composition provided both the antioxidant effect and a buffering effect and reduced the generation of impurities. The antioxidants tested prevented formation of USP Ropinirole Related Compound B. Citric acid functioned as both a buffer and an antioxidant, did not produce other the additional impurities seen with ascorbic acid and sodium metabisulfite.

To reduce oxidation, in addition to, or as an alternative to antioxidants, in some embodiments, the ropinirole composition can be mixed with the aqueous solvent under conditions where there is reduced or no oxygen in the environment. For example, the methods of making the ropinirole composition can occur for some or all of the process under an oxygen free environment, where there is less than about 20%, 15%, 10%, 5% or 1% oxygen in the manufacturing environment. In some embodiments, this can be achieved by manufacturing under vacuum conditions to remove the oxygen and/or by incorporating an inert gas, such as for example, nitrogen, argon, and/or helium in the environment. This will reduce oxidation of the ropinirole and its excipients. For example, oxygen can be removed when compounding and filling the container with the ropinirole composition by using an inert gas, such as for example, nitrogen, argon, and/or helium during manufacturing.

To reduce oxidation, in some embodiments, the ropinirole can be lyophilized. For example, after the ropinirole is dissolved in the aqueous solvent and additional additives are added (e.g., buffering agent, bulking agent, pH adjustment agent, antioxidant, preservative, etc.) and dissolved, the mixture can be lyophilized after the pH is adjusted. Typically, lyophilization includes freezing the ropinirole and then subjecting it to an intense vacuum to remove the ice to convert it into a dried cake or powder. This will reduce oxidation of the ropinirole composition and, thereby, reduce impurities in the final product. In some embodiments, when ropinirole hydrochloride is lyophilized, the ropinirole monohydrate is formed, which is suitable for injection.

Figure 2:
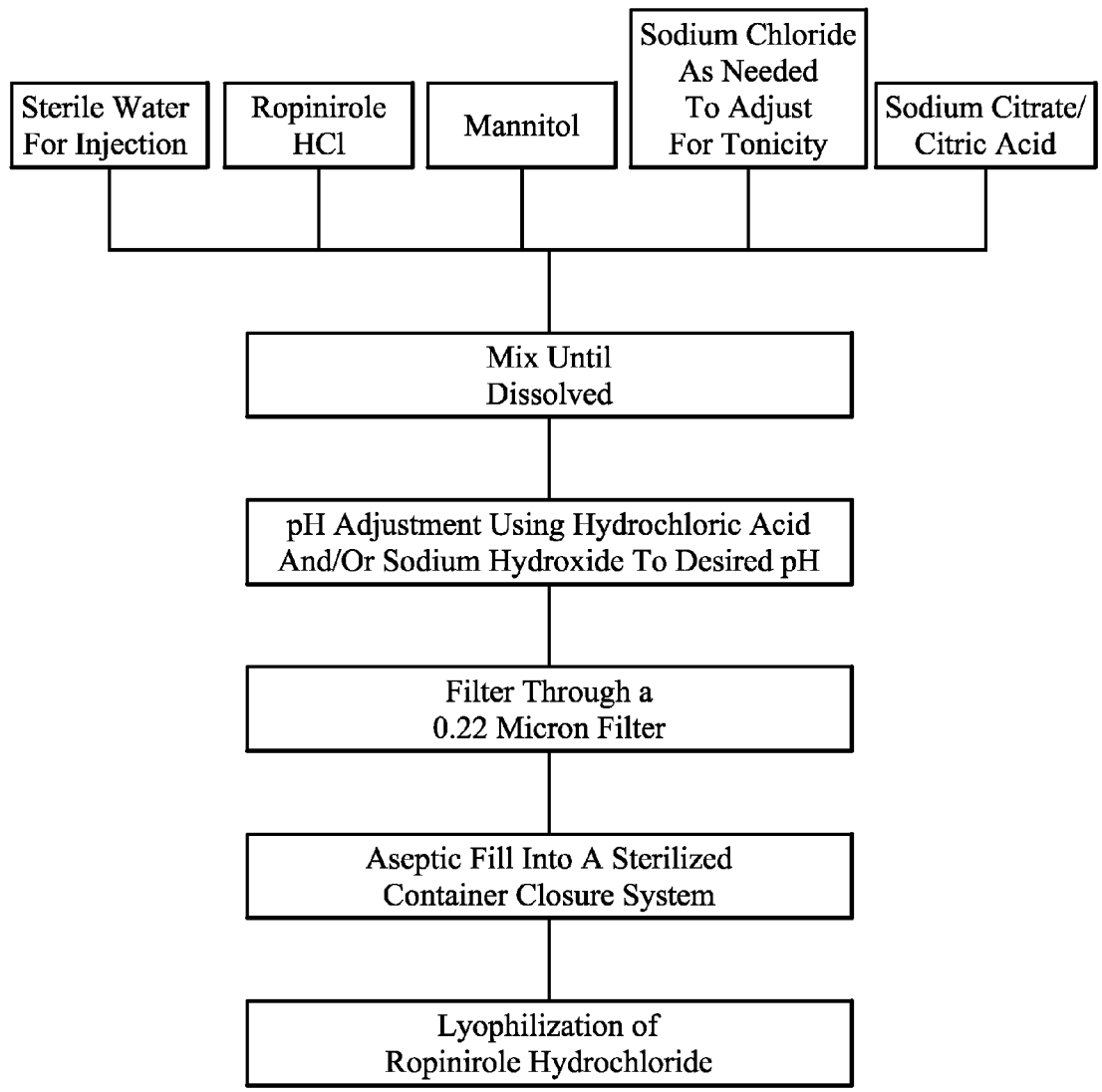
FIG. 2 is a flow diagram illustrating the steps to make sterilized and lyophilized ropinirole injection in accordance with one embodiment of the disclosure.

FIG. 2 is a flow diagram illustrating the steps to make sterilized and lyophilized ropinirole injection in accordance with one embodiment of the disclosure. The ropinirole is mixed with SWFI as the aqueous solvent, sodium chloride to adjust tonicity, mannitol as the bulking agent, and sodium citrate/citric acid as the buffer/antioxidant. Typically, in this embodiment, the pH is about 4.1 or about 4.2. The pH of the mixture is then adjusted with for example, hydrochloric acid and/or sodium hydroxide to the desired pH, which in this embodiment is about 4.4 to about 4.5. The pH-adjusted mixture is then filtered through a 0.22 micron filter to remove bacteria, other microbes, larger viruses and/or particulates. The filtered solution is then placed in a container suitable to store the composition and then the composition is lyophilized into a dry powder or cake. The lyophilized ropinirole composition can be reconstituted before injection with one or more of the aqueous solvents discussed above.

An exemplary sterilized and lyophilized ropinirole composition suitable for injection is listed in the Table B below.

TABLE B

Lyophilized Ropinirole Composition

| Ingredient | Purpose | Concentration mg/mL |
| --- | --- | --- |
| Ropinirole HCl | API | 15.0 |
| Citric Acid | Buffer/Antioxidant | 1.1 |
| Sodium Citrate | Buffer | 1.4 |
| Mannitol | Bulking agent | 50 |
| NaOH | pH adjustment | For pH adjustment |
| HCl | pH adjustment | For pH adjustment |
| Water for Injection | Solvent | QS to 1 mL |

Figure 10A:
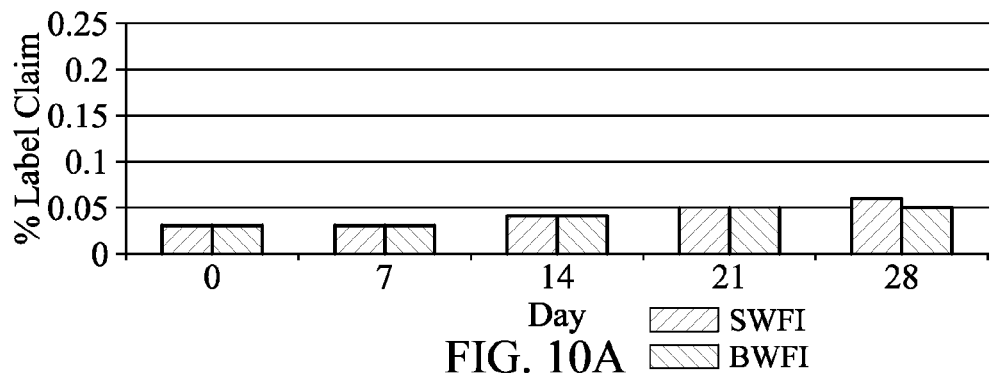
FIGS. 10A-10B are graphic illustrations showing the generation of impurities for sterilized and lyophilized injectable ropinirole after it has been reconstituted and stored for 28 days.
Figure 10B:
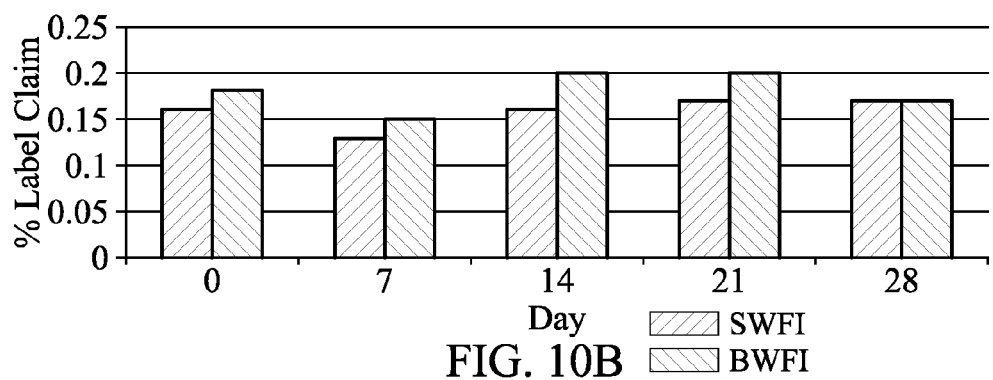

The lyophilized formulation of Table B and its impurities formed after reconstitution with SWFI at days 7, 14, 21 and 28 are shown in FIGS. 10A-10B.

The sterilized and stable ropinirole compositions of the present application can be provided in a medical package suitable for injection. In some embodiments, the medical package contains a solution that is compatible with the desired site of administration (e.g., intravenous administration). In some embodiments, the ropinirole formulation will be provided in a sterile, isotonic solution of ropinirole free of preservatives, where the composition does not contain any preservatives. In some embodiments, the ropinirole compositions can be provided containing preservatives.

The ropinirole formulations of the present application can be packaged in a pre-filled container that is ready for immediate delivery to an infusion device. The packaging includes a container filled with the ropinirole, a color coding system (label) for the various concentrations of the drug product and size of container, a package, a label, and instructions for use.

The term "pre-filled," as used herein, means containing an exact, pre-determined dose of a sterile pharmaceutical composition.

Treatment and Administration

The composition containing ropinirole may be used in treating or inhibiting disease or injury responsive to ropinirole therapy. The term "treatment" is used herein to characterize a process/method that is aimed at (1) delaying or preventing the onset of a disease state or condition; (2) slowing down or stopping the progression, aggravation or deterioration of the symptoms or signs of a clinical condition; (3) bringing about ameliorations of the symptoms or signs of the condition; and/or (4) curing the condition. The treatment may be administered before the onset of the condition for a prophylactic action or it may be administered after initiation of the condition for a therapeutic action.

Conditions suitable for treatment with the ropinirole compositions include Parkinson's disease, Restless Legs Syndrome (RLS), fibromyalgia, depression, hypertension, angina pectoris, congestive heart failure, kidney dysfunction, and/or chronic fatigue syndrome. In some embodiments, the ropinirole injection is used to treat Parkinson's disease.

In one embodiment, there is a method of treating Parkinson's disease in a patient suffering therefrom, the method comprising administering an injectable ropinirole composition comprising a therapeutically effective amount of ropinirole in an aqueous solvent, the composition having a pH of from about 3.0 to about 6.5. The ropinirole can be administered parenterally to bypass the gastrointestinal tract, which is often dysfunctional in Parkinson's disease. For example, the ropinirole compositions may be administered intravenously, subcutaneously, intramuscularly, intra-arterially, inthrathecally, epidurally, intraparenchymally, intraperitoneally, intracerebroventricularly, intraventricularly, etc., by infusion or injection to a patient. In one embodiment, the ropinirole composition is administered by subcutaneously implanted catheter and the drug delivered by a continuous or intermittent infusion.

A therapeutically effective amount of ropinirole can be administered to a patient in need of treatment. By "therapeutically effective amount", it is meant a dose of the drug that produces the effects for which it is administered. The exact dose will depend on the purpose of the treatment, and the particular patient. In some embodiments, ropinirole is delivered to a patient in a daily dose of between about 0.001 mg/kg/day to 100 mg/kg/day. A "patient" for the purposes of the present disclosure includes humans and other animals, particularly mammals including mice, rats, guinea pigs, rabbits, dogs, cats, swine, bovine, monkey, baboon, chimpanzee, or other organisms. Thus, the methods are applicable to both human therapy and veterinary applications. In a preferred embodiment the patient is a mammal, such as a human. Those "in need of treatment" include mammals already having the disease or disorder, as well as those prone to having the disease or disorder, including those in which the disease or disorder is to be prevented.

The ropinirole compositions of the current application allow for subsequent dilution by the addition of other components that may be simultaneously infused with the ropinirole. These include pain relieving medications suitable for combination with the ropinirole and include morphine, clonidine, hydromorphone, hydrocodone, meperidine, celecoxib, tramadol, oxycodone, acetaminophen, ketoprofen, ketorolac, ibuprofen, naproxen, or the like. It is appreciated in the art that other chemical compounds are similarly suitable for co-administration or separate administration with ropinirole in the current application.

In some embodiments, the ropinirole compositions can be administered by continuous infusion and/or intermittent infusion. Typically, continuous infusion includes a continual release of a stream of one or more therapeutic agents (e.g., ropinirole) over a predetermined time period and at a therapeutic level sufficient to achieve a desired therapeutic effect throughout the predetermined time period. Typically, intermittent infusion includes release of a stream of one or more therapeutic agents at a high rate in a bolus amount for a limited time period and at a therapeutic level sufficient to achieve a desired therapeutic effect.

In some embodiments, the ropinirole is administered by an infusion device. Any suitable infusion device may be used to deliver the composition containing ropinirole to a patient. The infusion device may be external to the patient or be an implantable infusion device including pumps. Suitable pumps for use with the injectable composition include an osmotic pump, a fixed rate or variable rate pump, a piston pump, a peristaltic pump, a patch pump, or the like.

Typically, infusion devices include reservoirs for housing the fluid formulation. A catheter is typically connected to the infusion device so that fluid from the reservoir may be pumped from the reservoir through the catheter to a targeted region of the patient. In some embodiments, the infusion device is implantable and includes a microprocessor for controlling the rate of delivery of the composition, which may be variable. In such embodiments, the implantable infusion device may communicate and receive infusion instructions from an external device, such as a physician programmer device. A suitable infusion device for use with the ropinirole compositions of the current application is an infusion device for subcutaneous infusion (e.g., a patch pump). In other embodiments, an implantable infusion device, such as Medtronic, Inc.'s SynchroMed II® can be used An alternative device that may be used for the delivery of the ropinirole includes, Medtronic Paradigm® REAL-Time Revel™ System, which may be adapted to deliver ropinirole.

In some embodiments, the injectable ropinirole composition of the present application can be administered with other oral and/or non-oral agents for the treatment of Parkinson's disease. Such agents include levodopa plus carbidopa (SINEMET®), levodopa plus controlled release carbidopa (SINEMET-CR®), levodopa plus benserazide (MADOPAR®), levodopa plus controlled release benserazide (MADOPAR-HBS); COMT (catechol-O-methyltransferase) inhibitors such as tolcapone and/or entacapone; dopamine agonists, such as bromocriptine, pergolide, ropinirole, pramipexole, lisuride, cabergoline, apomorphine, sumanirole, rotigotine, talipexole and dihydroergocriptine; and amantadine, adamantidine or a combination thereof. For example, the injectable ropinirole composition can be administered with conventional oral agents.

Having now generally described the application, the same may be more readily understood through the following reference to the following examples, which are provided by way of illustration and are not intended to limit the present application unless specified.

EXAMPLES

In the following examples, studies were performed and results obtained for determining suitable ropinirole compositions for injection. The pharmacokinetic and toxicological data for ropinirole was also tested.

Example 1

Degradation Products

Initial formulation development studies of ropinirole hydrochloride identified a degradant or impurity that develops over extended periods of time in aqueous and certain solvent systems acceptable for subcutaneous injections. The degradant was initially determined to be (4-[2-(dipropylamino)ethyl]indoline-2,3-dione hydrochloride) (USP Ropinirole Related Compound B) shown in reaction scheme I above based on HPLC analysis match of the impurity peak to reference standard retention time and UV spectra.

Example 2

Ropinirole Liquid for Injection

Ropinirole hydrochloride is compounded with excipients and sterile water for injection. FIG. 1 is a flow diagram illustrating the steps to make sterilized ropinirole injection in accordance with this example. The ropinirole is mixed with SWFI as the aqueous solvent, sodium chloride to adjust tonicity, and sodium citrate/citric acid as the buffer/antioxidant. Typically, in this embodiment, the pH is about 4.1 or about 4.2. The pH of the mixture is then adjusted with for example, hydrochloric acid and/or sodium hydroxide to the desired pH, which in this embodiment is about 4.3 to pH 4.4±0.1. The pH adjusted mixture is then filtered through a 0.22 micron filter and 3.4 mL is filled into 5 mL Type 1 glass vials, stoppered and capped with flip cap vial seals. The filtered solution is then placed in a container suitable to store the composition and then the composition is terminally sterilized. Table C lists the composition.

TABLE C

Sterile Liquid Ropinirole Composition

| Component | Grade | mg per mL | Function |
| --- | --- | --- | --- |
| Ropinirole Hydrochloride | USP | 15 mg | Active Ingredient |
| Sodium Chloride | USP, EP | 6 mg | Bulking Agent and tonicity adjustment |
| Sodium Citrate Dihydrate | USP, EP | 1.4 mg | Buffering Agent |
| Citric Acid Monohydrate | USP, EP | 1.1 mg | Buffering Agent/Antioxidant |
| Hydrochloric Acid | NF | As needed | pH Adjustment |
| Sodium Hydroxide | NF | As needed | pH Adjustment |
| Water for Injection | USP | QS | Solvent |

Example 3

Ropinerole pH and Stability

Ropinirole hydrochloride is compounded with excipients and sterile water for injection according to FIG. 1. The liquid ropinirole compositions contained citric acid and sodium citrate buffers/antioxidants and is shown in Table 1.

TABLE 1

Formulation summary

| Formulation | pH 4.4 (current) | pH 5.5 formulation | pH 7 formulation |
|---|---|---|---|
| Ropinirole HCl Drug Substance | 15 mg/mL | 15 mg/mL | 15 mg/mL |
| Citric Acid monosodium salt | 1.1 mg/mL | 0.5 mg/mL | — |
| Sodium Citrate dihydrate | 1.4 mg/mL | 2.2 mg/mL | 2.7 mg/mL |
| Sodium Chloride | 6 mg/mL | 6 mg/mL | 6 mg/mL |
| Barnstead Nanopure Water | Q.S. | Q.S. | Q.S. |
| Initial pH measurement | 4.3 | 5.5 | 7.3 |

These compositions were studied for stability and the presence of impurities (e.g., USP Ropinirole Related Compound B) over a 1 month to 6 month time period. The pH profile and the appearance of USP Ropinirole Related Compound B, other impurities, and the total impurities in weight % are shown below in Table D.

TABLE D

USP Ropinorole Related Compound B

|  | 1 month | 3 month | 6 month |
|---|---|---|---|
| pH 4.4 | 0.21 | 0.31 | 0.70 |
| pH 5.5 | 0.24 | 0.42 | 0.79 |
| pH 7 | 0.27 | 0.53 | 1.26 |
| Other Impurities | | | |
| pH 4.4 | 0.14 | 0.14 | 0.19 |
| pH 5.5 | 0.40 | 0.44 | 0.56 |
| pH 7 | 1.15 | 1.62 | 2.33 |
| Total Impurities | | | |
| pH 4.4 | 0.34 | 0.45 | 0.89 |
| pH 5.5 | 0.64 | 0.85 | 1.35 |
| pH 7 | 1.42 | 2.16 | 3.59 |

FIGS. 3A-3C are graphic illustrations showing the pH effect and the generation of impurities for sterilized injectable ropinirole mentioned in Table D. As the pH increases approaching 7.0, the amount of impurities increase, particularly USP Related Compound B impurity.

Example 4

Ropinirole with Antioxidants and Stability

Ropinirole hydrochloride is compounded with excipients and sterile water for injection according to FIG. 1. The liquid ropinirole compositions made were studied for stability and the presence of impurities (e.g., USP Ropinirole Related Compound B) over a 6 weeks period of time. The compositions contained different antioxidants. The appearance of USP Ropinirole Related Compound B, other impurities, and the total impurities in weight % are shown below in Tables E and F.

TABLE E

|  | Week 0 | Week 2 | Week 4 | Week 6 |
|---|---|---|---|---|
| DS SWFI | 0.05 | 0.05 | 0.04 | 0.05 |
| DS 1 mgNa2S2O5 | 0.05 | 0.05 | 0.05 | 0.05 |
| DS 2 mg Na2S2O5 | 0.05 | 0.04 | 0.05 | 0.05 |
| DS 3 mg Na2S2O5 | 0.04 | 0.04 | 0.04 | 0.05 |
| DS 2 mg AA | 0.17 | 0.21 | 0.21 | 0.26 |
| DS 10 mg AA | 0.11 | 0.19 | 0.24 | 0.27 |
| DS 20 mg AA | 0.10 | 0.16 | 0.20 | 0.19 |
| citrate buffer | 0.05 | 0.04 | 0.04 | 0.04 |
| RT 7.7 | | | | |
| DS SWFI | 0.08 | 0.08 | 0.08 | 0.08 |
| DS 1 mgNa2S2O5 | 0.08 | 0.08 | 0.09 | 0.09 |
| DS 2 mg Na2S2O5 | 0.08 | 0.09 | 0.09 | 0.09 |
| DS 3 mg Na2S2O5 | 0.09 | 0.10 | 0.09 | 0.09 |
| DS 2 mg AA | 0.34 | 0.40 | 0.42 | 0.45 |
| DS 10 mg AA | 0.31 | 0.42 | 0.44 | 0.46 |
| DS 20 mg AA | 0.29 | 0.16 | 0.42 | 0.43 |
| citrate buffer | 0.00 | 0.00 | 0.00 | 0.00 |
| Rel Comp A | | | | |
| DS SWFI | 0.00 | 0.00 | 0.00 | 0.00 |
| DS 1 mgNa2S2O5 | 0.10 | 0.30 | 0.42 | 0.45 |
| DS 2 mg Na2S2O5 | 0.08 | 0.30 | 0.40 | 0.44 |
| DS 3 mg Na2S2O5 | 0.10 | 0.33 | 0.46 | 0.48 |
| DS 2 mg AA | 0.68 | 0.81 | 0.81 | 0.84 |
| DS 10 mg AA | 0.41 | 0.62 | 0.64 | 0.65 |
| DS 20 mg AA | 0.37 | 0.54 | 0.56 | 0.57 |
| citrate buffer | 0.00 | 0.00 | 0.00 | 0.00 |
| Rel Comp B | | | | |
| DS SWFI | 0.24 | 0.62 | 0.98 | 1.19 |
| DS 1 mgNa2S2O5 | 0.12 | 0.12 | 0.16 | 0.17 |
| DS 2 mg Na2S2O5 | 0.11 | 0.10 | 0.12 | 0.13 |
| DS 3 mg Na2S2O5 | 0.10 | 0.09 | 0.11 | 0.12 |
| DS 2 mg AA | 0.18 | 0.20 | 0.17 | 0.15 |
| DS 10 mg AA | 0.04 | 0.00 | 0.00 | 0.00 |
| DS 20 mg AA | 0.02 | 0.00 | 0.00 | 0.00 |
| citrate buffer | 0.04 | 0.04 | 0.05 | 0.04 |
| RT 14.8 | | | | |
| DS SWFI | 0.00 | 0.00 | 0.00 | 0.00 |
| DS 1 mgNa2S2O5 | 0.88 | 0.64 | 0.20 | 0.23 |
| DS 2 mg Na2S2O5 | 2.02 | 1.92 | 1.27 | 1.25 |
| DS 3 mg Na2S2O5 | 3.40 | 3.15 | 2.27 | 2.37 |
| DS 2 mg AA | 0.00 | 0.00 | 0.00 | 0.00 |
| DS 10 mg AA | 0.03 | 0.00 | 0.00 | 0.00 |
| DS 20 mg AA | 0.00 | 0.00 | 0.00 | 0.00 |
| citrate buffer | 0.00 | 0.00 | 0.00 | 0.00 |

AA = ascorbic acid

TABLE F

Drug Substance + Sterile Water for Injection

|  | Week 0 | Week 2 | Week 4 | Week 6 |
|---|---|---|---|---|
| Drug Substance + Sterile Water for Injection | | | | |
| USP Ropinirole Related Compound B | 0.24 | 0.62 | 0.98 | 1.19 |
| Other Impurities | 0.12 | 0.12 | 0.12 | 0.12 |
| Total Impurities | 0.36 | 0.74 | 1.10 | 1.31 |
| Drug substance + Ascorbic Acid (AA) | | | | |
| USP Ropinirole Related Compound B | | | | |
| 2 mg/mL AA | 0.18 | 0.20 | 0.17 | 0.15 |
| 10 mg/mL AA | 0.04 | 0.00 | 0.00 | 0.00 |
| 20 mg/mL AA | 0.02 | 0.00 | 0.00 | 0.00 |
| Other Impurities | | | | |
| 2 mg/mL AA | 1.20 | 1.41 | 1.44 | 1.54 |
| 10 mg/mL AA | 0.87 | 1.23 | 1.32 | 1.38 |
| 20 mg/mL AA | 0.76 | 0.87 | 1.19 | 1.19 |

TABLE F-continued

Drug Substance + Sterile Water for Injection

|  | Week 0 | Week 2 | Week 4 | Week 6 |
|---|---|---|---|---|
| Total Impurities | | | | |
| 2 mg/mL AA | 1.37 | 1.62 | 1.61 | 1.69 |
| 10 mg/mL AA | 0.91 | 1.23 | 1.32 | 1.38 |
| 20 mg/mL AA | 0.78 | 0.87 | 1.19 | 1.19 |
| Drug substance + Sodium Metabisulfite ($Na_2S_2O_5$) | | | | |
| USP Ropinirole Related Compound B | | | | |
| 1 mg/mL $Na_2S_2O_5$ | 0.12 | 0.12 | 0.16 | 0.17 |
| 2 mg/mL $Na_2S_2O_5$ | 0.1 | 0.10 | 0.12 | 0.13 |
| 3 mg/mL $Na_2S_2O_5$ | 0.10 | 0.09 | 0.11 | 0.12 |
| Other Impurities | | | | |
| 1 mg/mL $Na_2S_2O_5$ | 1.11 | 1.06 | 0.76 | 0.82 |
| 2 mg/mL $Na_2S_2O_5$ | 2.23 | 2.35 | 1.80 | 1.83 |
| 3 mg/mL $Na_2S_2O_5$ | 3.64 | 3.63 | 2.86 | 2.99 |
| Total Impurities | | | | |
| 1 mg/mL $Na_2S_2O_5$ | 1.22 | 1.18 | 0.92 | 0.99 |
| 2 mg/mL $Na_2S_2O_5$ | 2.34 | 2.45 | 1.92 | 1.96 |
| 3 mg/mL $Na_2S_2O_5$ | 3.73 | 3.72 | 2.97 | 3.11 |
| Citrate buffered formulation (Lyophilized formulation reconstituted with SWFI) | | | | |
| USP Ropinirole Related Compound B | 0.04 | 0.04 | 0.05 | 0.04 |
| Other Impurities | 0.05 | 0.04 | 0.04 | 0.04 |
| Total Impurities | 0.08 | 0.09 | 0.09 | 0.08 |
| USP Ropinirole Related Compound B | | | | |
| DS + SWFI | 0.24 | 0.62 | 0.98 | 1.19 |
| DS + 20 mg/mL AA | 0.02 | 0.00 | 0.00 | 0.00 |
| DS + 1 mg/mL Na2S2O5 | 0.12 | 0.12 | 0.16 | 0.17 |
| Citrate buffered formulation | 0.04 | 0.04 | 0.05 | 0.04 |
| Other Impurities | | | | |
| DS + SWFI | 0.12 | 0.12 | 0.12 | 0.12 |
| DS + 20 mg/mL AA | 0.76 | 0.87 | 1.19 | 1.19 |
| DS + 1 mg/mL Na2S2O5 | 1.11 | 1.06 | 0.76 | 0.82 |
| Citrate buffered formulation | 0.05 | 0.04 | 0.04 | 0.04 |
| Total Impurities | | | | |
| DS + SWFI | 0.36 | 0.74 | 1.10 | 1.31 |
| DS + 20 mg/mL AA | 0.78 | 0.74 | 1.19 | 1.19 |
| DS + 1 mg/mL Na2S2O5 | 1.22 | 1.18 | 0.92 | 0.99 |
| Citrate buffered formulation | 0.08 | 0.09 | 0.09 | 0.08 |

The ascorbic acid can be in the composition in an amount of from about 2 mg/ml to about 10 mg/ml or 20 mg/ml. The sodium metabisulfite can be in the composition in an amount of from about 1 mg/ml to about 2 mg/ml or 3 mg/ml.

Figure 4:
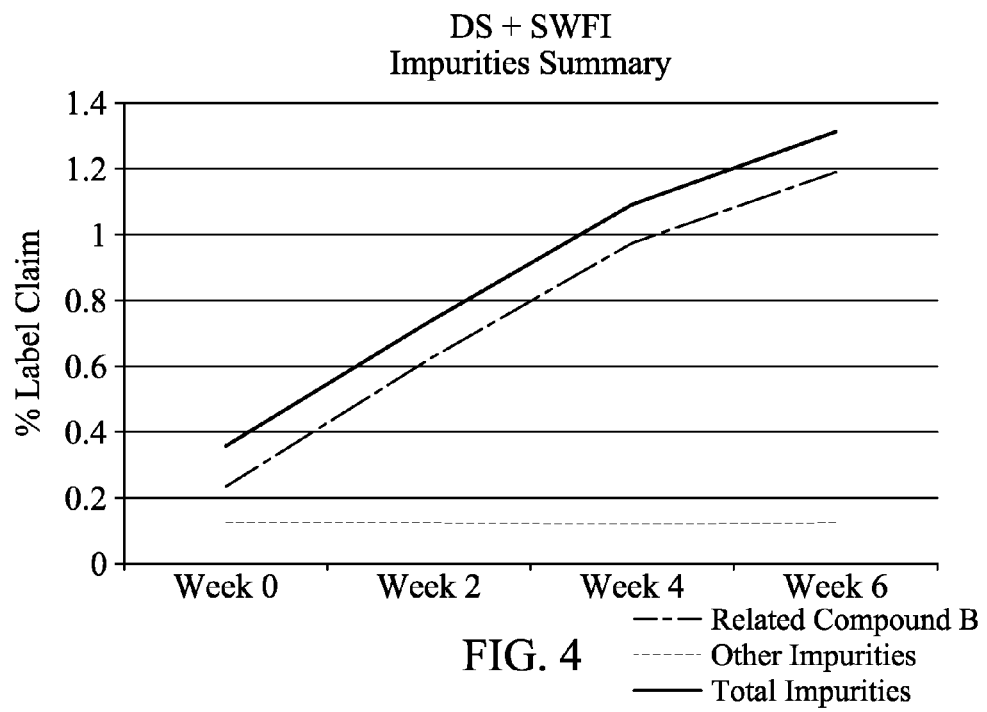
FIG. 4 is a graphic illustration showing the generation of impurities for sterilized injectable ropinirole in sterile water for injection.
Figure 5:
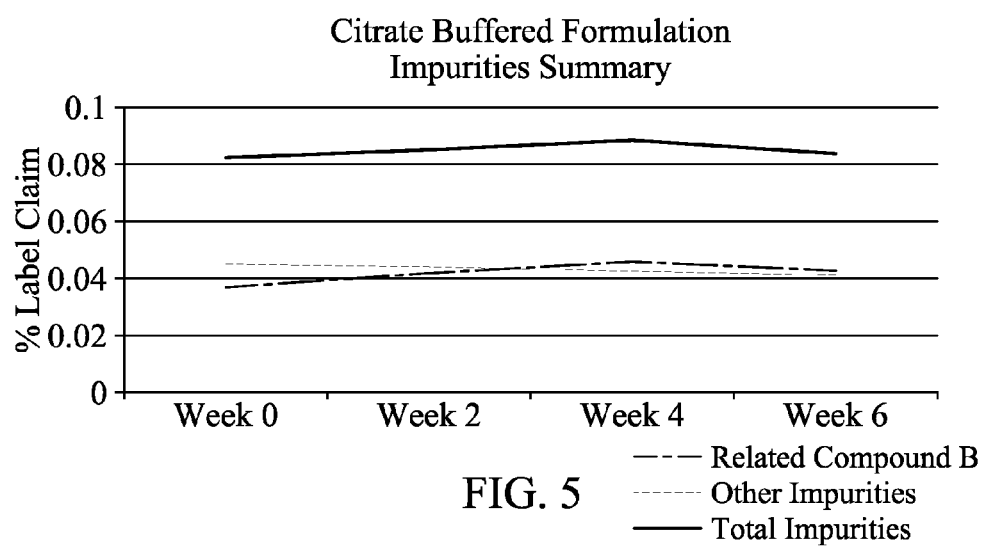
FIG. 5 is a graphic illustration showing the generation of impurities for sterilized injectable ropinirole with a citrate buffer and citric acid, which can also function as an antioxidant in the composition.
Figure 6A:
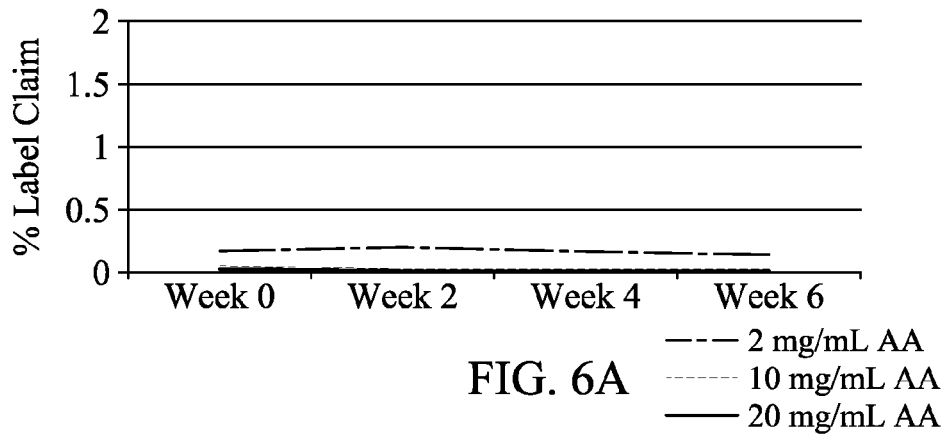
FIGS. 6A-6C are graphic illustrations showing the generation of impurities for sterilized injectable ropinirole containing the anti-oxidant ascorbic acid in the composition.
Figure 6B:
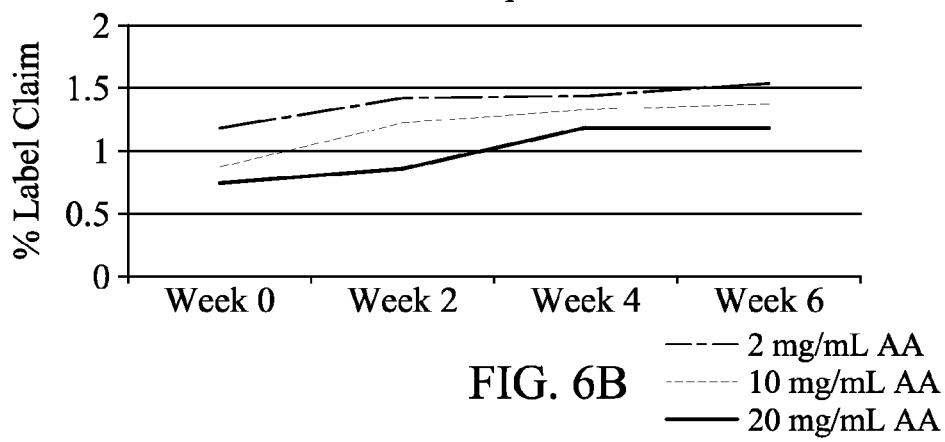
Figure 6C:
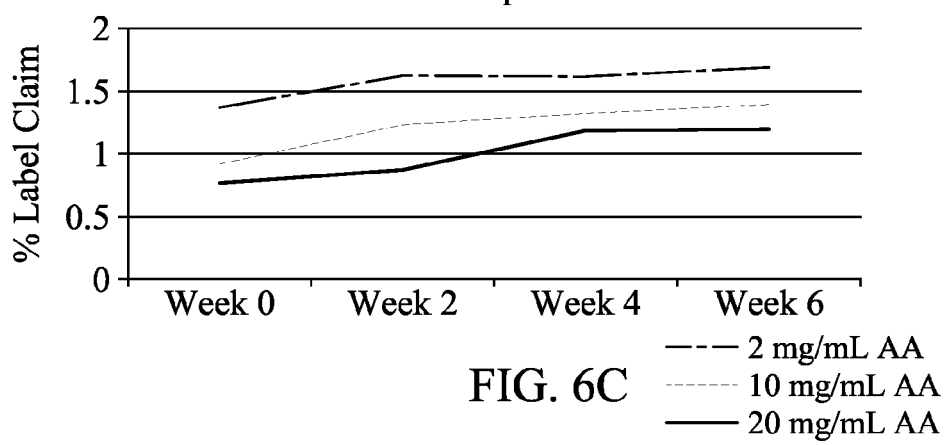
Figure 7A:
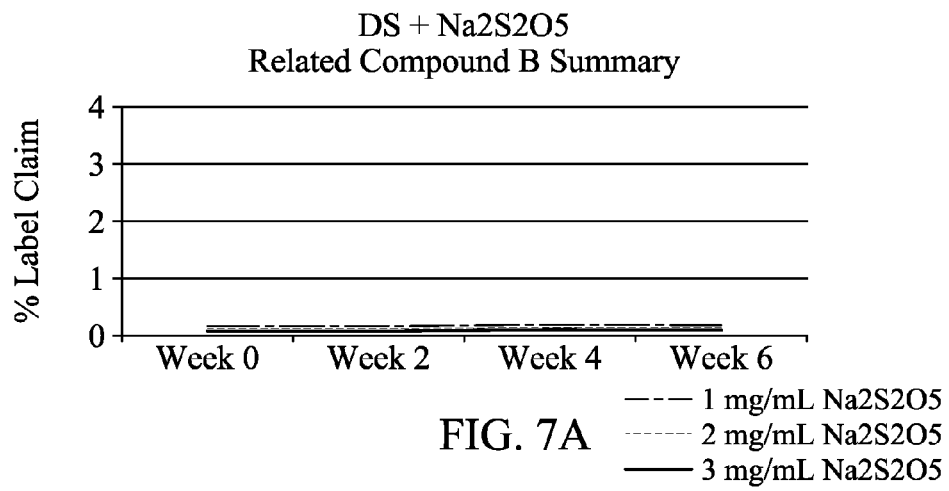
FIGS. 7A-7C are graphic illustrations showing the generation of impurities for sterilized injectable ropinirole containing the anti-oxidant sodium metabisulfite in the composition.
Figure 7B:
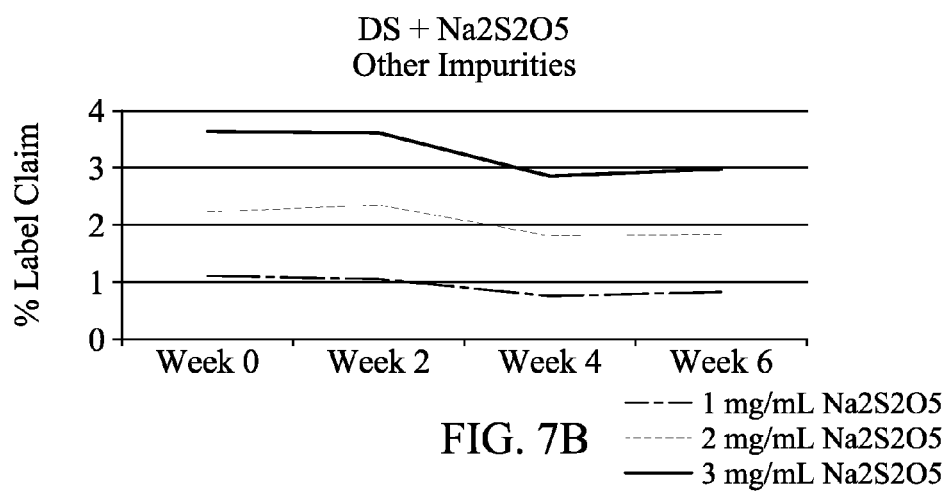
Figure 7C:
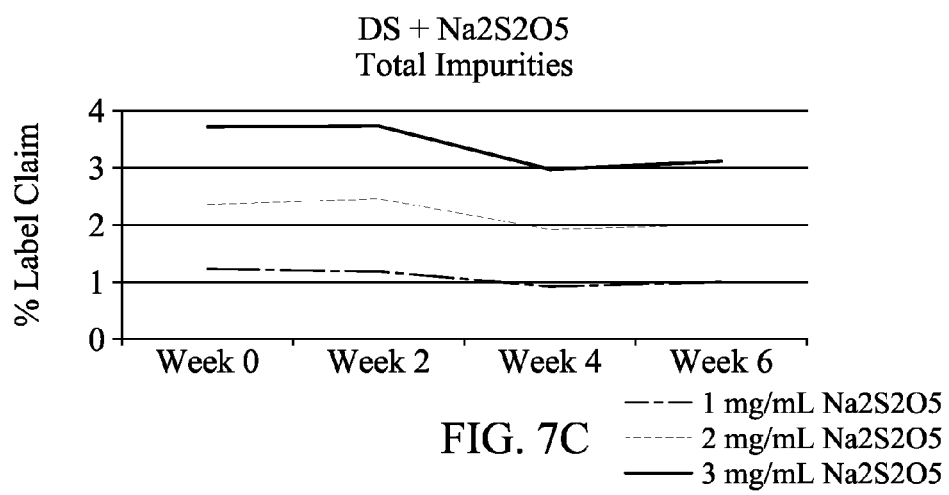
Figure 8A:
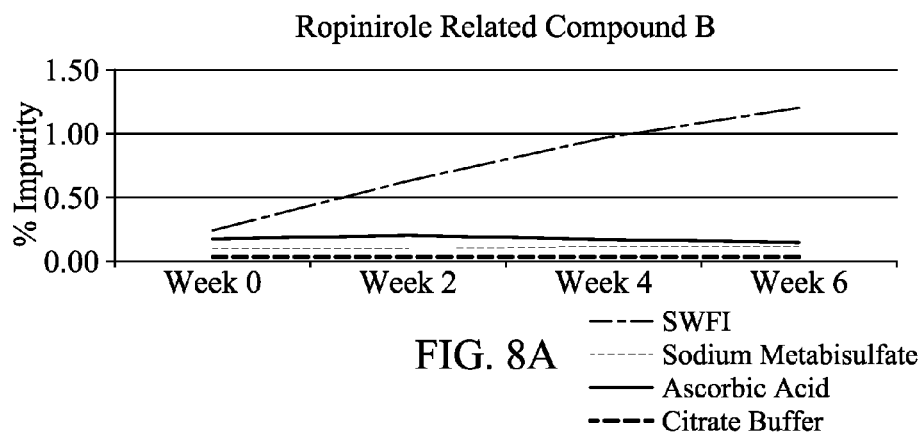
FIGS. 8A-8C are graphic illustrations comparing the generation of impurities for sterilized injectable ropinirole containing different antioxidants.
Figure 8B:
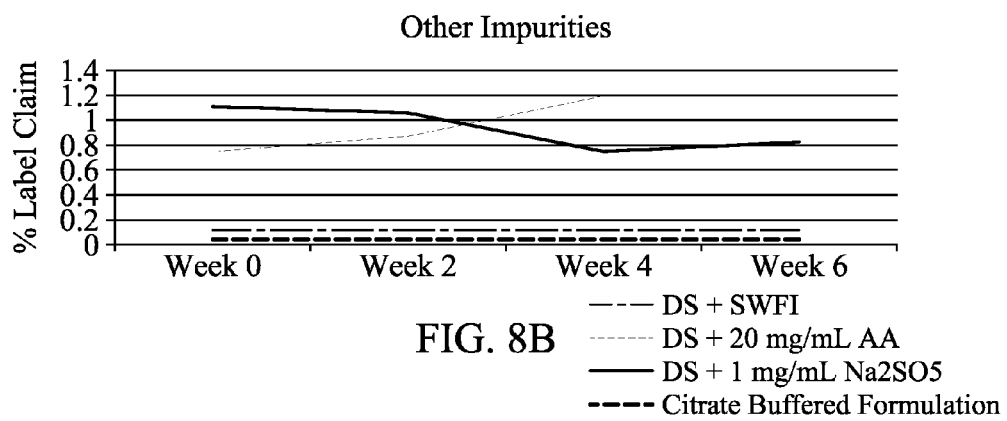
Figure 8C:
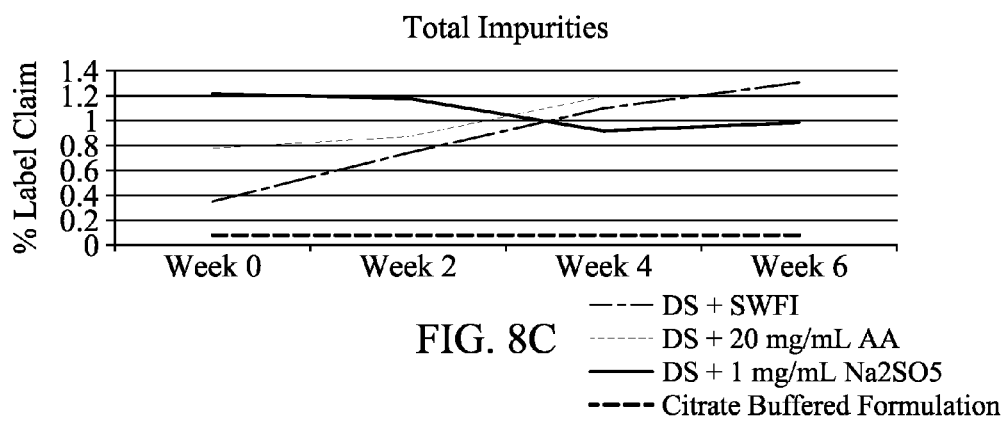

FIG. 4 is a graphic illustration showing the generation of impurities from Tables E and/or F for sterilized injectable ropinirole in sterile water for injection. FIG. 5 is a graphic illustration showing the generation of impurities from Tables E and/or F for sterilized injectable ropinirole with a citrate buffer in the composition. FIGS. 6A-6C are graphic illustrations showing the generation of impurities from Tables E and/or F for sterilized injectable ropinirole containing the anti-oxidant ascorbic acid in the composition. FIGS. 7A-7C are graphic illustrations showing the generation of impurities from Tables E and/or F for sterilized injectable ropinirole containing the anti-oxidant sodium metabisulfite in the composition. FIGS. 8A-8C are graphic illustrations comparing the generation of impurities from Tables E and/or F for sterilized injectable ropinirole containing different antioxidants. It was found that 1) the highest concentration of ascorbic acid (20 mg/ml) had the least amount of impurities in the composition; 2) the highest concentration of sodium metabisulfite (3 mg/ml) had the least amount of related USP Ropinirole Related Compound B, but most other impurities in the composition; and (3) the sterilized injectable ropinirole compositions containing citrate were the most stable and had the least generation of impurities.

Example 5

Ropinirole hydrochloride is compounded with excipients and sterile water for injection according to FIG. 1. The liquid ropinirole compositions shown in Table A above were stored at 25° C. with 60% room humidity and at 5° C. The ropinirole compositions made were studied for stability and the presence of impurities (e.g., USP Ropinirole Related Compound B) over 1 week to 18 months period of time. The results are shown in Table G.

TABLE G

|  | assay | Imp | Rel comp A | Rel comp B | Other Impurities | Total |
|---|---|---|---|---|---|---|
| 25° C./60% RH | | | | | | |
| Initial (CYR59) | 100.1 | 0.1 | <0.1 | <0.1 | 0.1 | 0.1 |
| 7 Day (CYR60) | 99.5 | 0.1 | <0.1 | <0.1 | 0.1 | 0.1 |
| 14 Day (CYR62) | 99.1 | 0.1 | <0.1 | <0.1 | 0.1 | 0.1 |
| 1 Month (CYR64) | 98.5 | 0.1 | <0.1 | 0.07 | 0.1 | 0.2 |
| 3 Month (CYR65) | 99.4 | 0.1 | <0.1 | 0.16 | 0.1 | 0.3 |
| 6 Month (CYR67) | 99.6 | 0.1 | <0.1 | 0.29 | 0.1 | 0.4 |
| 12 Month (00298-001) | 99.8 | 0.11 | <0.1 | 0.64 | 0.11 | 0.8 |
| 18 Month (00298-002) | 97.7 | 0.11 | <0.1 | 0.85 | 0.11 | 1 |
| 5° C. | | | | | | |
| 7 Day (CYR60) | 99.1 | 0.1 | <0.1 | <0.1 | 0.1 | 0.1 |
| 14 Day (CYR62) | 99.6 | 0.1 | <0.1 | <0.1 | 0.1 | 0.1 |
| 1 Month (CYR64) | 98.4 | 0.1 | <0.1 | <0.1 | 0.1 | 0.1 |
| 3 Month (CYR65) | 99.9 | 0.1 | <0.1 | 0.06 | 0.1 | 0.2 |
| 6 Month (CYR67) | 98.9 | 0.1 | <0.1 | 0.07 | 0.1 | 0.2 |
| 12 Month (00298-001) | 100.6 | 0.1 | <0.1 | 0.12 | 0.1 | 0.2 |
| 18 Month (00298-002) | 98.8 | 0.1 | <0.1 | 0.17 | 0.1 | 0.3 |

Figure 9A:
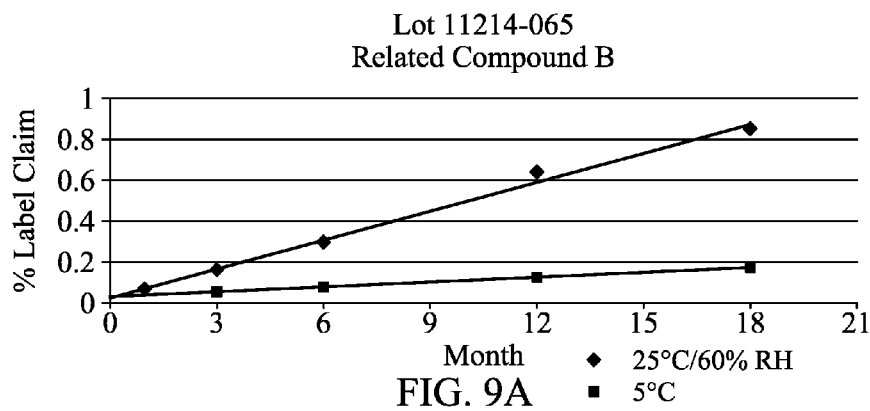
FIGS. 9A-C are graphic illustrations showing the generation of impurities for sterilized injectable ropinirole 15 mg/mL containing the citrate buffer and citric acid over an 18 month period at room temperature and under refrigeration.
Figure 9B:
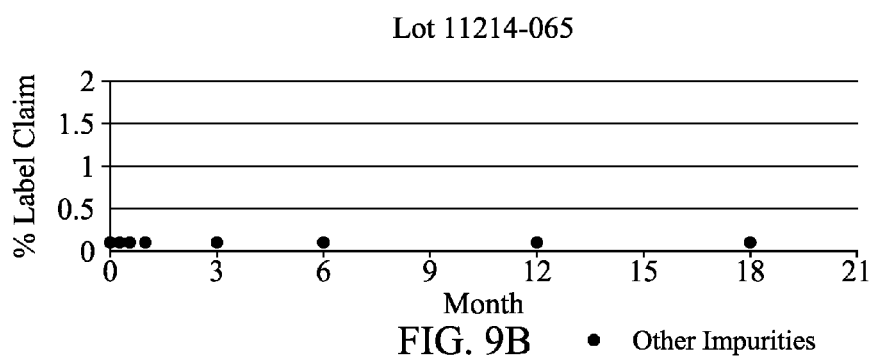
Figure 9C:
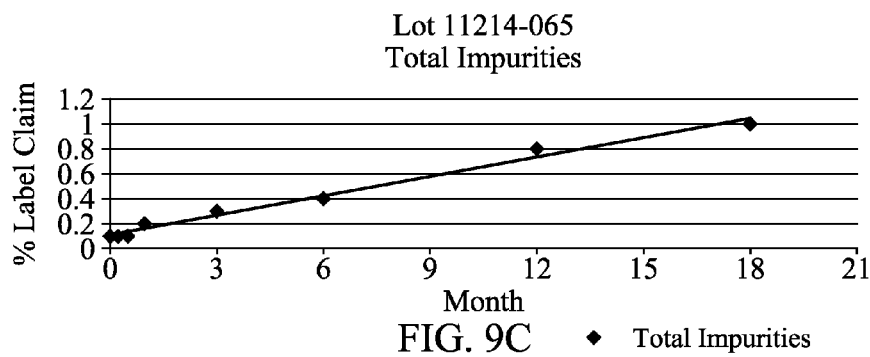
Figure 9D:
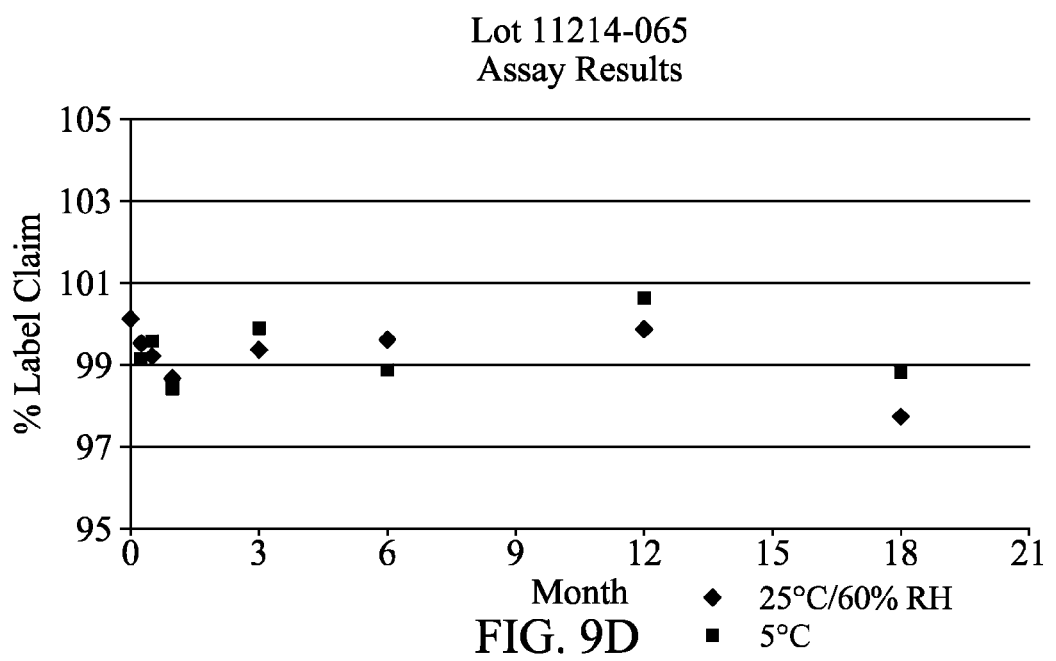
FIG. 9D is a graphic illustration of the potency of sterilized injectable ropinirole 15 mg/mL that is maintained over an 18-month period at room temperature and under refrigeration.

FIGS. 9A-C are graphic illustrations showing the generation of impurities for sterilized injectable ropinirole 15 mg/mL containing the citrate buffer over an 18 month period at room temperature and under refrigeration listed in Tables A and G. FIG. 9D is a graphic illustration of the potency of sterilized injectable ropinirole 15 mg/mL that is maintained over a 12 month period at room temperature and under refrigeration listed in Tables A and G. The compositions were stable and maintained their potency for at least 18 months with few impurities generated. The compositions stored at 5° C. under refrigeration were the most stable and had the fewest impurities generated.

Example 6

Lyophilized Ropinirole

A 28 day reconstitution study at 25° C. for injectable ropinirole was initiated. The formulation is shown in Table B above. The purpose of this study was to observe the degradation profile based on an anticipated product administration period (i.e., a pharmacist preparing a month's supply of vials and a patient administering one vial over a three day period and exhausting the supply of prepared dosages over a month). FIG. 2 is a flow diagram illustrating the steps to make sterilized and lyophilized ropinirole injection in accordance with one embodiment of the disclosure. The ropinirole is mixed with SWFI or Bacteriostatic Water for injection (BWFI) as the aqueous solvent, sodium chloride to adjust tonicity, mannitol as the bulking agent, and sodium citrate/citric acid as the buffer/antioxidant. Typically, in this embodiment, the pH is about 4.0 or about 4.1. The pH of the mixture is then adjusted with for example, hydrochloric acid and/or sodium hydroxide to the desired pH, which in this embodiment is about 4.4 to about 4.5. The pH adjusted mixture is then filtered through a 0.22 micron filter. The filtered solution is then placed in a container suitable to store the composition and then the composition is lyophilized into a dry powder or cake. The lyophilized ropinirole composition can be reconstituted before injection with one or more of the aqueous solvents discussed above. The stability results are shown in Table H.

TABLE H

Lyophilized Ropinirole –28 Day Stability

| | Day | | | | |
|---|---|---|---|---|---|
| | 0 | 7 | 14 | 21 | 28 |
| USP Ropinirole Related Compound B | | | | | |
| SWFI | 0.03 | 0.03 | 0.04 | 0.05 | 0.06 |
| BWFI | 0.03 | 0.03 | 0.04 | 0.05 | 0.05 |
| Total Impurities | | | | | |
| SWFI | 0.16 | 0.13 | 0.16 | 0.17 | 0.17 |
| BWFI | 0.18 | 0.15 | 0.2 | 0.2 | 0.17 |

FIGS. 10A-10B are graphic illustrations showing the generation of impurities for sterilized and lyophilized injectable ropinirole after it has been reconstituted and stored for 28 days. The one observation of the lyophilized formulation versus early liquid formulation development was the reduced levels of USP Related Compound B [(4-[2-(Dipropylamino) ethyl]indoline-2,3-dione hydrochloride)]. This reduced impurity level of Ropinirole HCl USP Ropinirole Related Compound B in the lyophilized formulation resulted in challenging that Ropinirole HCl USP Related Compound B was caused by an oxidation process versus a hydrolytic process based on the absence of oxygen in the lyophilized material. Oxygen is not present in the lyophilized material because a) the lyophilization chamber is under vacuum thus removing in the lyophilization change; b) any dissolved oxygen in the liquid phased is removed during freeze drying performed under vacuum; and c) the lyophilization chamber is backfilled with nitrogen to break vacuum after the vials are stoppered.

Example 7

Liquid Ropinirole

Ropinirole HCl was prepared using a liquid formulation approach, minimizing oxygen levels during compounding, filling the liquid formulation into vials and terminally sterilizing the product at 121.1° C. for 20 minutes. The results of this study are shown in Table 2.

TABLE 2

Liquid Formulation Stability Results (25° C./65% RH)

| Time Point | % USP Related Compound B |
|---|---|
| Initial | <0.1% |
| 7 day | <0.1% |

TABLE 2-continued

Liquid Formulation Stability Results (25° C./65% RH)

| Time Point | % USP Related Compound B |
|---|---|
| 14 day | <0.1% |
| 1 Month | 0.07% |
| 3 Month | 0.16% |
| 6 Month | 0.29% |

From Table 2, the amount of USP Ropinirole Related Compound B increased from a 1 month to a 6 month period. It was decided to add an antioxidant sodium metabisulfite and ascorbic acid. Results of the impurity profiles were determined. It was observed that ropinirole related compound B can be significantly reduced over time by the addition of an antioxidant. However, additional impurities are created based on the use of an antioxidant. The means to minimize and prevent creation of additional new impurities and minimize USP Ropinirole Related Compound B levels is by removing oxygen in the liquid formulation prior to filling a container closure system and blanketing the container closure system with an inert gas such as nitrogen or argon to displace oxygen that may be in the container closure prior to being filled with a liquid.

Example 8

Lyophilization of Ropinirole

TABLE I

| Lyophilization Condition/Time point | Assay | Active Pharmaceutical Ingredient Supplier Impurity | Rel Comp A | Rel Comp B | Largest Unknown | Total |
|---|---|---|---|---|---|---|
| Initial 25° C./60% RH | 100.7 | <0.1 | <0.1 | ND | NR | <0.1 |
| 1 month | 102.8 | <0.1 | <0.1 | <0.1 | 0.07 | 0.1 |
| 3 month | 100.5 | <0.1 | <0.1 | <0.1 | 0.06 | 0.1 |
| 6 month | 100.8 | <0.1 | <0.1 | <0.1 | <0.1 | <0.1 |
| 12 month | 102 | <0.1 | <0.1 | <0.1 | <0.1 | <0.1 |
| 18 month | 101.2 | <0.1 | <0.1 | <0.1 | 0.06 | 0.1 |
| 40° C./75% RH | | | | | | |
| 2 week | 100.2 | <0.1 | <0.1 | <0.1 | 0.06 | 0.1 |
| 1 month | 102.1 | <0.1 | <0.1 | <0.1 | 0.07 | 0.1 |
| 2 month | 100.2 | <0.1 | <0.1 | <0.1 | 0.06 | 0.1 |
| 3 month | 101.1 | <0.1 | <0.1 | <0.1 | 0.06 | 0.1 |
| 6 month | 101.4 | <0.1 | <0.1 | <0.1 | <0.1 | <0.1 |

From Table I, lyophilized ropinirole maintained its potency at time periods from 1 to 6 months at 25° C. and 40° C. The amount of USP Ropinirole Related Compound B formed was less than 1%.

Example 9

Liquid Ropinirole Storage in Vials

TABLE J

|  | assay | Imp | Rel comp A | Rel comp B | Other Impurities | Total |
|---|---|---|---|---|---|---|
| Inverted results | | | | | | |
| 25° C./60% RH | | | | | | |
| Initial | 100.3 | <0.1 | <0.1 | <0.1 | <0.1 | <0.1 |
| 3 Month | 99.4 | <0.1 | <0.1 | 0.12 | <0.1 | 0.1 |
| 40° C./75% RH | | | | | | |
| 1 Month | 97.7 | <0.1 | <0.1 | 0.12 | <0.1 | 0.1 |
| 3 Month | 99.6 | <0.1 | <0.1 | 0.43 | <0.1 | 0.4 |
| USP Ropinirole Related Compound B | | | | | | |
|  | 0 | 1 | 3 | | | |
| 25° C./60% RH | 0 |  | 0.12 | | | |
| 40° C./75% RH | 0 | 0.12 | 0.43 | | | |
| Upright results | | | | | | |
| 25° C./60% RH | | | | | | |
| Initial | 100.3 | <0.1 | <0.1 | <0.1 | <0.1 | <0.1 |
| 3 Month | 99.9 | <0.1 | <0.1 | 0.11 | <0.1 | 0.1 |
| 40° C./75% RH | | | | | | |
| 1 Month | 97.6 | <0.1 | <0.1 | 0.13 | <0.1 | 0.1 |
| 3 Month | 98.9 | <0.1 | <0.1 | 0.42 | <0.1 | 0.4 |

From Table J, ropinirole liquid maintained its potency at time periods from 1 to 3 months at 25° C. and 40° C. The amount of USP Ropinirole Related Compound B formed was less than 1%.

Example 10

Figure 11A:
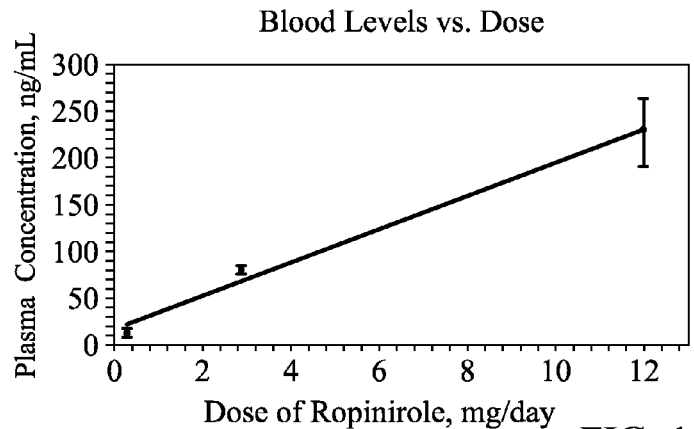
FIGS. 11A-11C are graphic illustrations showing dose and blood levels of sterilized injectable ropinirole administered subcutaneously in rats, rabbits, and minipigs.
Figure 11B:
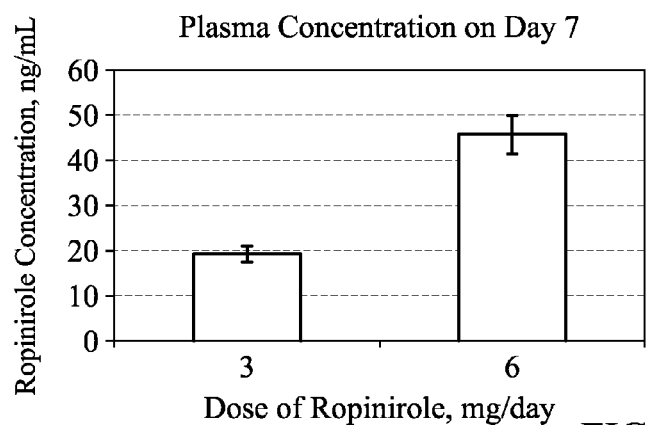
Figure 11C:
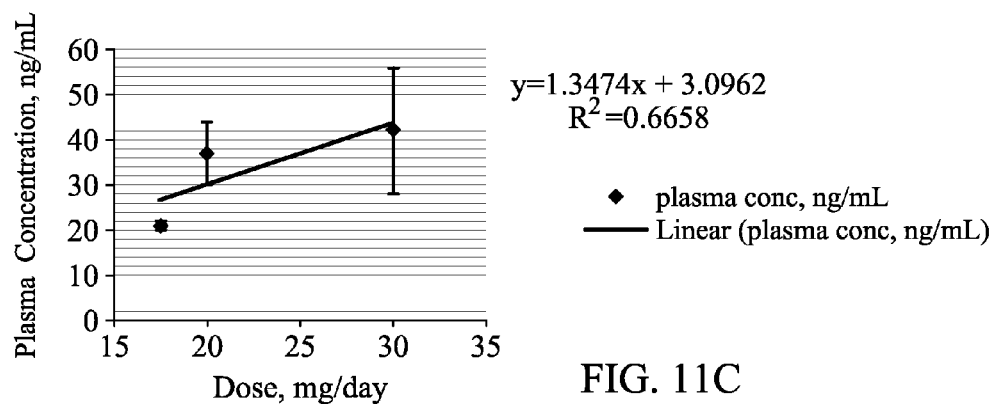

Pharmacokinetics (PK) of Injectable Ropinirole Administered Subcutaneously in Rats, Rabbits, and Minipigs The PK of ropinirole at steady state levels was tested in rats (FIG. 11A), rabbits (FIG. 11B) and minipigs (FIG. 11C). The rats were given sterilized ropinirole HCl in sterile water for injection, no excipients. The rabbits were given lyophilized ropinirole HCl reconstituted with BWFI or SWFI to a final concentration of 15 mg/ml, where the formulation was the same as Table B. The minipigs were given ropinirole 15 mg/ml, which was terminally sterilized, where the formulation was the same as Table A. Animal subjects were injected with a sterilized injectable ropinirole composition. Administration produced steady state plasma levels of ropinirole that demonstrated an approximate linear relationship to the dose administered. These results show that the injectable ropinirole composition can safely be administered to non-human mammals.

Example 11

Toxicology Studies in Rats, Rabbits and Minipigs

Ropinirole Injectable Administration

Figure 12:
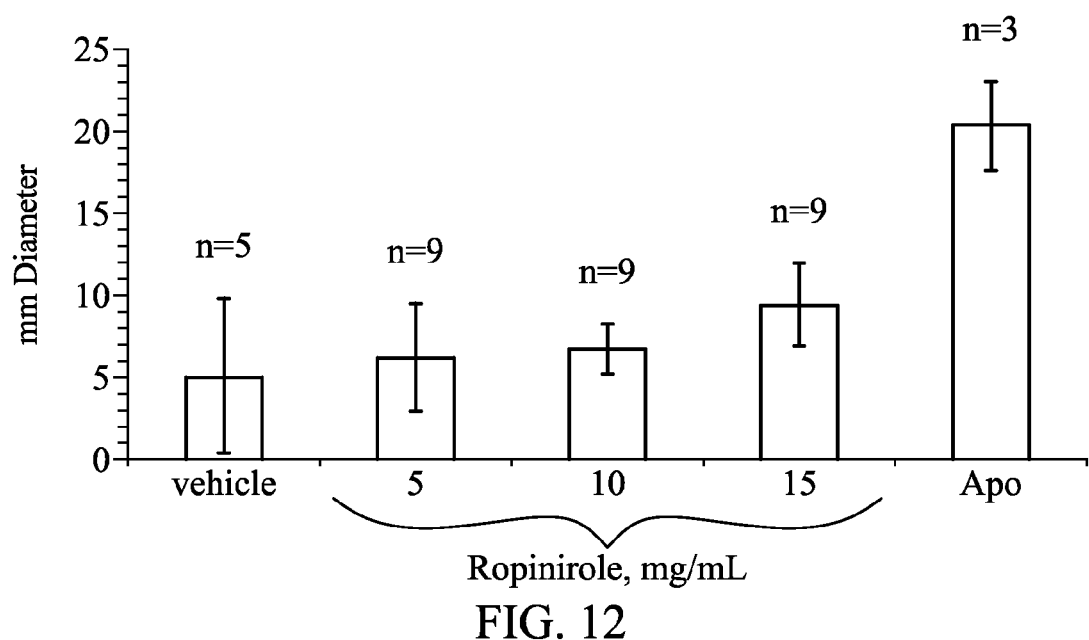
FIG. 12 is a graphic illustration of reaction site diameters to sterilized ropinirole injection tested in animals.

Toxicology was tested on rats, rabbits and minipigs. A sterilized injectable ropinirole composition at 15 mg/mL/day was administered to the rabbits and minipigs. Injection sites were administered 1 mL of infusate per day for 3 days and tissues collected immediately after cessation of delivery. Sterilized apomorphine was administered to the minipig subjects at a relatively low clinically relevant dose (10 mg/3 mL/day) and produced a reaction that was approximately twice as large as 15 mg/mL/day ropinirole. The results show that ropinirole causes mild inflammation/necrosis at the site of infusion. The reactions at the local sites of infusion are not detectable grossly at the surface of the skin but only at the level of the cannula tip in the subcutis upon microscopic evaluation. A slight trend towards larger reactions with higher concentrations/doses of ropinirole relative to vehicle-treated sites was found but was concluded to be much less severe than apomorphine-induced inflammation at clinically relevant doses (FIGS. 12 and 13).

Histopathology Score

Figure 13:
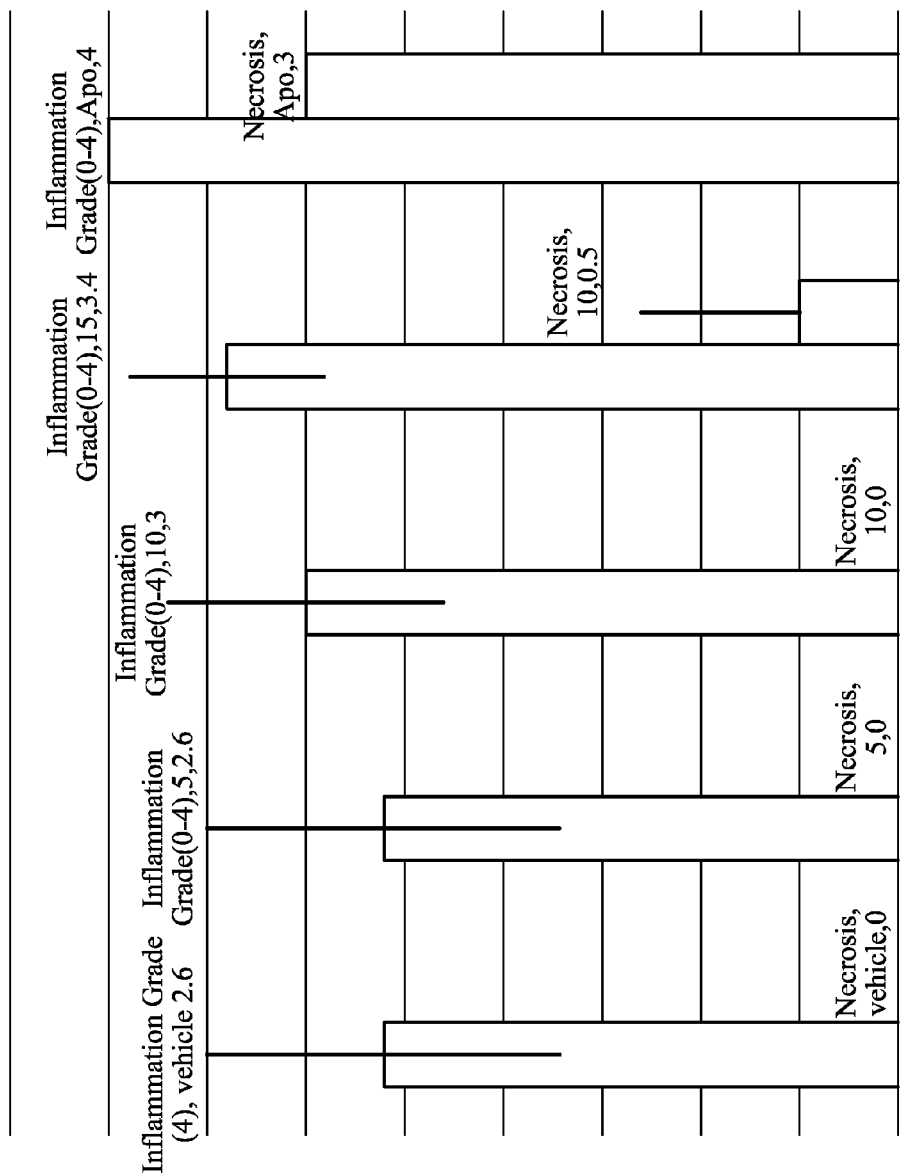
FIG. 13 is a graphic illustration of inflammation and necrosis scores for sites given 3 days of infusion of the delivery vehicle, sterilized ropinirole injection and sterilized apomorphine injection in animals.
Figure 14:
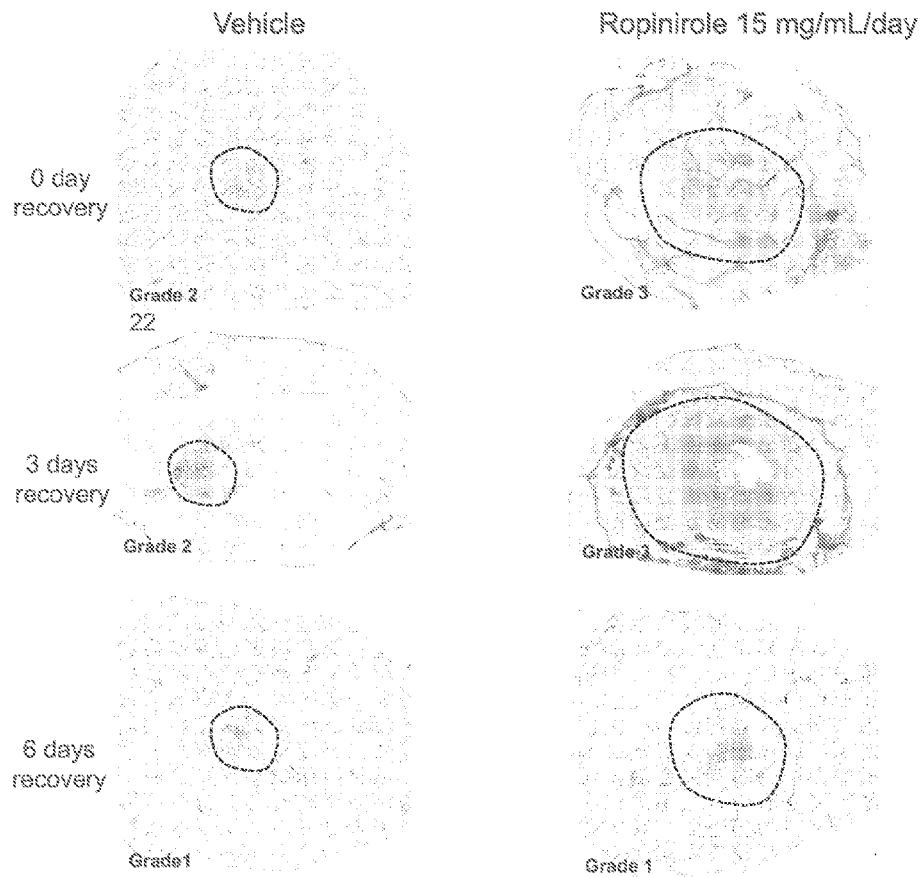
FIG. 14 are photomicrographs showing the changes in site reaction from subcutaneously administered ropinirole injection and its delivery vehicle over time.

The ropinirole delivered at 15 mg/mL/day produced a site that was limited to the local area of the cannula tip and healed extensively over 6 days (FIG. 13). When administered repeatedly to the same site of infusion (3 days of infusion followed by 3 days of no infusion followed by 3 days of infusion with a new infusion set), two and three repeat administrations did not differ significantly from sites treated with a single 3-day administration. A 0-4 scoring system (0=none, 1=minimal, 2=mild, 3=moderate, 4=severe) was used to grade the site reactions in the subcutis at the level of the cannula tip as viewed microscopically. Apomorphine consistently produced severe inflammation and moderate necrosis. Ropinirole produced moderate-to-severe inflammation and minimal-to-mild necrosis at 15 mg/mL/day. Ropinirole at 5 mg/mL/day produced inflammation (mild-to-moderate) equivalent to vehicle.

Example 12

Contemplated Preclinical and Clinical Strategies for Ropinirole Human Dosing Preclinical Dosing In order to reduce side effects upon initiation of oral therapy, ropinirole is titrated over several weeks to months to achieve the ultimate therapeutic dose. A similar although possibly abbreviated titration scheme is anticipated for the injectable formulation. (See Table K). From a volume-delivered perspective, 15 mg/mL appears to be an ideal dosage strength.

TABLE K

Anticipated Human (Subcutaneous) SQ Ropinirole Dosing and Titration

| | Titration Dosing, mg/day | | Daily SQ Volume, mL | |
|---|---|---|---|---|
| Time, weeks | Oral | SQ | 15 mg/mL ropinirole | 5 mg/mL ropinirole |
| 1 | 0.75 | 0.41 | 27.3 | 82 |
| 2 | 1.5 | 0.83 | 55.3 | 166 |
| 3 | 2.25 | 1.24 | 82.7 | 248 |
| 4 | 3.0 | 1.65 | 110 | 330 |
| 5 | 4.5 | 2.48 | 165.3 | 496 |
| 6 | 6.0 | 3.30 | 220.0 | 660 |
| 7 | 7.5 | 4.13 | 275.3 | 826 |
| 8 | 9.0 | 4.95 | 330.0 | 990 |
| 9 | 12 | 6.60 | 440.0 | 1320 |
| 10 | 15 | 8.25 | 550.0 | 1650 |
| 11 | 18 | 9.90 | 660.0 | 1980 |

TABLE K-continued

Anticipated Human (Subcutaneous) SQ Ropinirole Dosing and Titration

| Time, weeks | Titration Dosing, mg/day Oral | Titration Dosing, mg/day SQ | Daily SQ Volume, mL 15 mg/mL ropinirole | Daily SQ Volume, mL 5 mg/mL ropinirole |
|---|---|---|---|---|
| 12 | 21 | 11.55 | 770.0 | 2310 |
| 13 | 24 | 13.20 | 880.0 | 2640 |

Clinical Dosing

Clinical studies will administer continuous SQ infusion of ropinirole. In initial clinical studies, the infusion will begin at an infusion rate delivering a total of 0.5 mg ropinirole to a single site over 72 hours. This is one fourth of the usual starting dose of 2 mg/day for patients beginning therapy with oral extended release ropinirole. The ropinirole dose will be escalated by increasing the infusion rate every 72 hours as follows:

Dose 1: The infusion will begin at a dose of 0.5 mg/day (solution of ropinirole 15 mg/mL infused at a rate of 34 μL/day) and continued for 72 hrs.

Dose 2: After 72 hours, the infusion site will be changed and then the infusion will be increased to a dose of 1.0 mg/day (solution of ropinirole 15 mg/mL infused at a rate of 67 μL/day) for the next 72 hrs.

Dose 3: The infusion site will be changed and the infusion will be increased to a dose of 2.0 mg/day (solution of ropinirole 15 mg/mL infused at a rate of 133 μL/day) for 72 hrs. The vehicle infusion rate will be escalated as per ropinirole at 34, 67, and 133 μL/day.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A stable injectable ropinirole composition comprising a therapeutically effective amount of ropinirole solubilized in an aqueous solvent to form a solution, the composition having a pH of from about 3.0 to about 6.5, wherein the solution comprises a sterilized solution of ropinirole hydrochloride in an amount of about 1 mg/mL to about 133 mg/mL and the composition comprises less than about 3.0% by weight of (4-[2-(dipropylamino)ethyl]indoline-2,3-dione hydrochloride) after about 30 days to about 36 months of storage at room temperature.

2. An injectable ropinirole composition according to claim 1, wherein the composition further comprises at least one buffering agent, a bulking agent, pH adjustment agent, or antioxidant.

3. An injectable ropinirole composition according to claim 1, wherein the composition comprises less than 3% by weight of impurities and is prepared in a substantially oxygen-free environment.

4. An injectable ropinirole composition according to claim 1, wherein the composition comprises from about 0.07 to about 2.5% by weight of (4-[2-(dipropylamino)ethyl]indoline-2,3-dione hydrochloride) after 30 days to about 36 months of storage at room temperature.

5. An injectable ropinirole composition according to claim 1, wherein the pH of the composition is from about 3.5 to about 5.5 and the composition is preservative-free.

6. An injectable ropinirole composition according to claim 2, wherein (i) the bulking agent comprises sodium chloride or mannitol; (ii) the buffering agent comprises sodium citrate and/or citric acid; (iii) the pH adjustment agent comprises hydrochloric acid and/or sodium hydroxide; and/or (iv) the antioxidant comprises ascorbic acid, sodium metabisulfite, and/or a citrate.

7. An injectable ropinirole composition according to claim 1, wherein the sterilized solution of ropinirole hydrochloride is terminally sterilized and comprises a preservative.

8. An injectable ropinirole composition according to claim 2, wherein the bulking agent comprises mannitol.

9. A method of preparing the sterilized injectable ropinirole composition according to claim 1, the method comprising adjusting a pH of ropinirole in an aqueous solvent to between about 3.0 to about 6.5, wherein the concentration of ropinirole in the aqueous solvent is between 1 mg/mL and 133 mg/mL; and heat sterilizing the pH adjusted ropinirole to achieve a sterility assurance level of $1 \times 10^6$ or $1 \times 10^{12}$ so as to form a terminally sterilized injectable ropinirole composition having less than about 3% by weight of (4-[2-(dipropylamino)ethyl]indoline-2,3-dione hydrochloride) based on a total weight of ropinirole in the composition.

10. A method according to claim 9, wherein the composition comprises from about 0.07 to about 2.5% by weight of (4-[2-(dipropylamino)ethyl]indoline-2,3-dione hydrochloride) after 30 days to about 36 months of storage at room temperature.

11. A method according to claim 9, wherein the pH is from about 3.5 to about 5.5 and the composition is preservative-free.

12. A method according to claim 9, wherein the pH adjusted ropinirole is filtered before steam sterilization.

13. A method according to claim 9, wherein the composition further comprises at least one buffering agent, a bulking agent, pH adjustment agent, or antioxidant.

14. A method according to claim 13, wherein (i) the bulking agent comprises sodium chloride or mannitol; (ii) the buffering agent comprises sodium citrate and/or citric acid; (iii) the pH adjustment agent comprises hydrochloric acid and/or sodium hydroxide; and/or (iv) the antioxidant comprises ascorbic acid, sodium metabisulfite, and/or a citrate.

15. A method of treating Parkinson's disease in a patient suffering therefrom, the method comprising administering an injectable ropinirole composition of claim 1.

16. A method according to claim 15, wherein the composition is administered parenterally to the patient.

17. A method according to claim 16, wherein the composition is administered intravenously, subcutaneously or intramuscularly to the patient.

18. A method according to claim 16, wherein the composition is administered by a continuous subcutaneous infusion or intermittent subcutaneous infusion to the patient via an infusion pump.

19. A method according to claim 15, wherein the injectable ropinirole composition comprises at least one buffering agent, a bulking agent, pH adjustment agent, or antioxidant.

20. An injectable ropinirole composition according to claim 1, wherein the composition further comprises a pH adjustment agent.

21. An injectable ropinirole composition according to claim 1, wherein the composition further comprises an antioxidant.

22. An injectable ropinirole composition according to claim 1, wherein the composition further comprises a buffering agent.

23. An injectable ropinirole composition according to claim 1, wherein the composition comprises less than about 0.07% to about 2.5% by weight of (4-[2-(dipropylamino)ethyl]indoline-2,3-dione hydrochloride) after about 30 days to about 36 months of storage.

* * * * *